US012580082B2

(12) United States Patent
Barkfors et al.

(10) Patent No.: US 12,580,082 B2
(45) Date of Patent: Mar. 17, 2026

(54) PAIN MANAGEMENT SYSTEM

(71) Applicant: PAINDRAINER AB, Lund (SE)

(72) Inventors: Mats Göran Barkfors, Lund (SE); Maria Linnea Elisabeth Rosén Klement, Lund (SE); Carl Arne Krister Borrebaeck, Lund (SE)

(73) Assignee: PAINDRAINER AB (SE)

( * ) Notice: Subject to any disclaimer, the term of this patent is extended or adjusted under 35 U.S.C. 154(b) by 465 days.

(21) Appl. No.: 18/017,539

(22) PCT Filed: Jul. 26, 2021

(86) PCT No.: PCT/EP2021/070869
§ 371 (c)(1),
(2) Date: Jan. 23, 2023

(87) PCT Pub. No.: WO2022/018300
PCT Pub. Date: Jan. 27, 2022

(65) Prior Publication Data
US 2023/0268075 A1 Aug. 24, 2023

(30) Foreign Application Priority Data

Jul. 24, 2020 (GB) ...................................... 2011500

(51) Int. Cl.
*G16H 50/30* (2018.01)
(52) U.S. Cl.
CPC ................................... *G16H 50/30* (2018.01)
(58) Field of Classification Search
CPC ...................................................... G16H 50/30
See application file for complete search history.

(56) References Cited

U.S. PATENT DOCUMENTS

| | | |
|---|---|---|
| 7,463,927 B1 | 12/2008 | Chaouat |
| 10,102,341 B2 | 10/2018 | Moturu et al. |
| 10,383,571 B1 * | 8/2019 | Pulliam ................... A61B 5/11 |

(Continued)

OTHER PUBLICATIONS

International Search Report and Written Opinion for PCT/EP2021/070869, dated Jan. 27, 2022.

(Continued)

*Primary Examiner* — Michael I Ezewoko
(74) *Attorney, Agent, or Firm* — Billion & Armitage

(57) ABSTRACT

A pain-management system (300) configured to: receive a target-pain-score (314) that represents a level of pain that the user considers acceptable during a defined period of time: receive one or more target-input-parameters (304) which represent properties and/or activities of a user during the same defined period of time, wherein the one or more target-input-parameters (314) are a subset of a full list of input-parameters that are available: receive one or more settings (315) that represent one or more input-parameters that are to be increased or decreased: use a neural network that has been trained for the individual user to determine one or more calculated-user-parameters (316) based on the target-get-pain-score (314) and the target-input-parameters (304), wherein at least one of the calculated-user-parameters (316) is set based on the settings (315); and present the one or more calculated-user-parameters (316) using a user interface.

17 Claims, 18 Drawing Sheets

(56) References Cited

U.S. PATENT DOCUMENTS

| | | | |
|---|---|---|---|
| 10,898,718 B2 * | 1/2021 | Srivastava | A61N 1/36071 |
| 11,123,562 B1 * | 9/2021 | Pulliam | A61N 1/36071 |
| 11,399,762 B1 * | 8/2022 | Feuer | A61B 5/0022 |
| 11,850,427 B2 * | 12/2023 | Rezai | G16H 20/30 |
| 2002/0107434 A1 * | 8/2002 | Lange | A61B 5/291 |
| | | | 702/124 |
| 2014/0088990 A1 * | 3/2014 | Nawana | G16H 40/40 |
| | | | 705/2 |
| 2014/0276188 A1 | 9/2014 | Jardin | |
| 2016/0005320 A1 | 1/2016 | Decharms et al. | |
| 2019/0022397 A1 * | 1/2019 | Srivastava | A61N 1/36139 |

OTHER PUBLICATIONS

Summons to attend oral proceedings for Application No. 21755700.
8; mailed on Oct. 20, 2023; 7 pages.

* cited by examiner

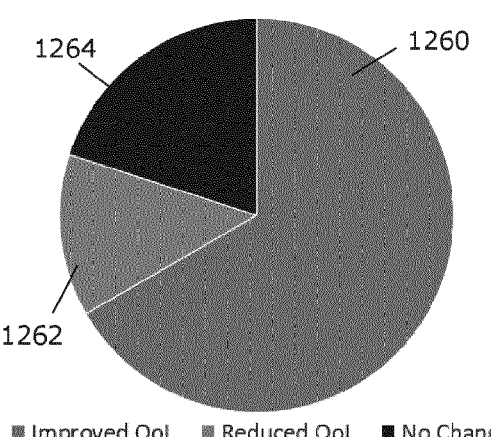

Change in Pain Interferance

■ Improved QoL  ■ Reduced QoL  ■ No Change

The relation between responding and non-responding patients, regarding improved Pain Interference (QoL).

FIG. 12

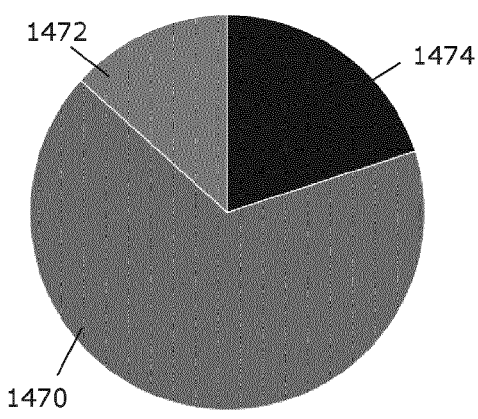

Change in Pain Intensity

■ No Change  ■ Reduced Pain  ■ Increased Pain

The relation between responding and non-responding patients regarding improved Pain Intensity.

FIG. 14

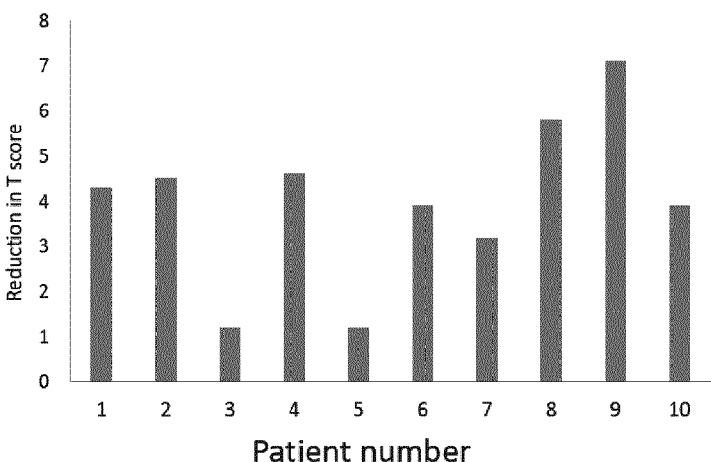

Patient number

Differences (reduction) in T-scores in Pain Interference (QoL), for responding patients in study phase one (patient 1 to 5) and phase two (patient 6 to 10).

FIG. 13

PAIN MANAGEMENT SYSTEM

The present disclosure relates to pain management system that can be used by a user to monitor and predict chronic pain based on their activities that they perform.

According to a first aspect, there is provided a pain-management system configured to:

receive a target-pain-score that represents a level of pain that the user considers acceptable during a defined period of time;

receive one or more target-input-parameters which represent properties and/or activities of a user during the same defined period of time, wherein the one or more target-input-parameters are a subset of a full list of input-parameters that are available;

receive one or more settings that represent one or more input-parameters that are to be increased or decreased;

use a neural network that has been trained for the individual user to determine one or more calculated-user-parameters based on the target-pain-score and the target-input-parameters, wherein at least one of the calculated-user-parameters is set based on the settings; and present the one or more calculated-user-parameters using a user interface.

Advantageously, such a system can guide the user to change their behaviours in a way that improves their health and wellbeing with a reduced likelihood of exceeding a pain limit of their choosing. This can greatly increase a user's/patient's quality of life (QoL).

The system may be configured to:

inspect a set of historic pain-parameter-log-entries associated with the user to identify, as a matched-pain-parameters-log-entry, a pain-parameters-log-entry that is a match with the received target-pain-score and the target-input-parameters, wherein each pain-parameter-log-entry represents a plurality of user-input-parameters and a user-input pain-score;

modify the matched-pain-parameters-log-entry based on the settings in order to generate a modified-pain-parameters-log-entry;

apply the neural network to the modified-pain-parameters-log-entry to determine a calculated-pain-score; and present, using the user interface: (i) one or more user-parameters of the modified-pain-parameters-log-entry as the calculated-user-parameters, and (ii) the calculated-pain-score.

The system may be configured to modify the matched-pain-parameters-log-entry to generate the modified-pain-parameters-log-entry by increasing or decreasing one or more user-input-parameters of the matched-pain-parameters-log-entry.

The system may be configured to:

inspect a set of historic pain-parameter-log-entries associated with the user to identify, as a matched-pain-parameters-log-entry, a pain-parameters-log-entry that is a match with the received target-pain-score and the target-input-parameters, wherein each pain-parameter-log-entry represents a plurality of user-input-parameters and a user-input pain-score;

modify the matched-pain-parameters-log-entry based on the settings in order to generate a modified-pain-parameters-log-entry;

apply the neural network to the modified-pain-parameters-log-entry to determine a calculated-pain-score; and compare the calculated-pain-score to the target-pain-score, and:

if the calculated-pain-score is greater than the target-pain-score, then:

adjust one or more of the input-parameters of the modified-pain-parameters-log-entry;

apply the neural network to the adjusted modified-pain-parameters-log-entry to determine an adjusted calculated-pain-score; and repeat the compare step one or more times for the adjusted calculated-pain-score; and if the calculated-pain-score is less than or equal to the target-pain-score, then present using the user interface: (i) one or more user-parameters of the modified-pain-parameters-log-entry as the calculated-user-parameters, and (ii) the calculated-pain-score.

The system may be configured to repeat the compare step a plurality of times up to a predetermined maximum number. The predetermined maximum number may vary over time.

The system may be further configured to:

present to the user via the user interface an option for modifying one or more of the calculated-user-parameters;

receive one or more modified calculated-user-parameters from the user interface representative of user input;

apply the neural network to the modified calculated-user-parameters to determine a modified calculated-pain-score; and present the modified calculated-pain-score using the user interface.

The system may further comprise:

a user interface configured to receive:

a plurality of user-input-parameters, which represent properties and/or activities of a user during a defined period of time; and a user-input pain-score, which represents a degree of pain experienced by the user during the same defined period of time; and an AI processor configured to:

set a plurality of weighting-values of the neural network based on the plurality of user-input-parameters and the user-input pain-score for the user.

The system may be configured to store the plurality of weighting-values associated with a user-identifier, wherein the user-identifier is uniquely associated with an individual user's profile.

The system may be further configured to:

modify the functionality of the user interface over time such that the user is presented with additional mechanisms for providing the user-input-parameters.

The user-input-parameters and/or the target-input-parameters may include one or more of the following characteristics:

(i) a duration-characteristic, which represents the duration that the user performed the activity/or exhibited the property;

(ii) an intensity-characteristic, which represents the intensity with which the user performed the activity;

(iii) a satisfaction-characteristic, which represents the degree of satisfaction that the user experienced when performing the activity; and (iv) a type-characteristic.

The AI processor may be configured to store pain-parameters-log-entries in memory, wherein each pain-parameters-log-entry comprises:

the plurality of user-input-parameters;

the user-input-pain-score; and a date-identifier associated with the corresponding user-input-parameters and user-input pain-score.

Each pain-parameters-log-entry may further comprise:

a user-identifier that is uniquely associated with an individual user for which the plurality of user-input-parameters and the user-input-pain-score relates.

The system may be configured to determine a pain trigger by:

processing a plurality of pain-parameter-log-entries to identify pain-parameter-log-entries that have a user-input pain-score that is increasing (or above a high-pain-trigger-threshold) as high-pain-parameter-log-entries, wherein each pain-parameter-log-entry comprises one or more user-input-parameters and a user-input pain-score;

perform an analysis of the user-input-parameters of the high-pain-parameter-log-entries to determine a correlation-score that represents the degree of correlation between values of corresponding user-input-parameters in the high-pain-parameter-log-entries; and identify one or more user-parameters as a pain trigger if they have a correlation-score that satisfies a correlation-criterion.

The system may be configured to determine a pain protector by:

processing a plurality of pain-parameter-log-entries to identify pain-parameter-log-entries that have a user-input pain-score that is decreasing (or lower than a low-pain-trigger-threshold) as low-pain-parameter-log-entries, wherein each pain-parameter-log-entry comprises one or more user-input-parameters and a user-input pain-score;

perform an analysis of the user-input-parameters of the low-pain-parameter-log-entries to determine a correlation-score that represents the degree of correlation between values of corresponding user-input-parameters in the low-pain-parameter-log-entries; and identify one or more user-parameters as a pain protector if they have a correlation-score that satisfies a correlation-criterion.

The plurality of user-input-parameters may comprise one or more sensed-input-parameters. The sensed-input-parameters may be provided directly or indirectly from a sensor.

The user-input-parameters may comprise one or more of:

a sleep-parameter;
a work-parameter;
a physical-activity-parameter;
a housework-parameter;
a leisure-parameter;
a rest-parameter; and
a pain-range-parameter;
a heart-rate-parameter;
a blood-pressure-parameter;
a temperature-parameter;
an energy/tiredness level parameter; and/or
a stress level parameter.

There is also disclosed a computer-implemented method comprising:

receiving a target-pain-score that represents a level of pain that the user considers acceptable during a defined period of time;

receiving one or more target-input-parameters which represent properties and/or activities of a user during the same defined period of time, wherein the one or more target-input-parameters are a subset of a full list of input-parameters that are available;

receiving one or more settings that represent one or more input-parameters that the user is looking to increase or decrease;

using a neural network that has been trained for the individual user to determine one or more calculated-user-parameters based on the target-pain-score and the target-input-parameters, wherein at least one of the calculated-user-parameters is set based on the settings; and presenting the one or more calculated-user-parameters using a user interface.

There is also provided a pain-management system comprising:

a user interface configured to receive:

a plurality of user-input-parameters, which represent properties and/or activities of a user during a defined period of time; and a user-input pain-score, which represents a degree of pain experienced by the user during the same defined period of time;

an AI processor that is configured to:

set a plurality of weighting-values of a neural network based on the plurality of user-input-parameters and the user-input pain-score for the user.

Such a system can include any of the features and functionality that are described herein.

There is also disclosed a personal-management system configured to:

receive a target-score that represents a score/level of a personal-characteristic that the user considers acceptable during a defined period of time;

receive one or more target-input-parameters which represent properties and/or activities of a user during the same defined period of time (the one or more target-input-parameters may be a subset of a full list of input-parameters that are available);

receive one or more settings that represent one or more input-parameters that are to be increased or decreased;

use a neural network that has been trained for the/each individual user to determine one or more calculated-user-parameters based on the target-score and the target-input-parameters, wherein at least one of the calculated-user-parameters is set based on the settings; and present the one or more calculated-user-parameters using a user interface.

There is also disclosed a computer-implemented method comprising:

receiving a target-score that represents a score/level of a personal-characteristic that the/each user considers acceptable during a defined period of time;

receiving one or more target-input-parameters which represent properties and/or activities of the/each user during the same defined period of time (the one or more target-input-parameters can be a subset of a full list of input-parameters that are available);

receiving one or more settings that represent one or more input-parameters that the user is looking to increase or decrease;

using a neural network that has been trained for the individual user to determine one or more calculated-user-parameters based on the target-score and the target-input-parameters, wherein at least one of the calculated-user-parameters is set based on the settings; and presenting the one or more calculated-user-parameters using a user interface.

There is also disclosed a personal-management system comprising:

a user interface configured to receive:

a plurality of user-input-parameters, which represent properties and/or activities of a user during a defined period of time; and a user-input-score, which represents a score/level of a personal-characteristic experienced by the user during the same defined period of time;

an AI processor that is configured to:

set a plurality of weighting-values of a neural network based on the plurality of user-input-parameters and the user-input-score for the user.

Such systems and methods can provide a platform that can guide the user to change their behaviours in a way that improves their health and wellbeing with a reduced likelihood of exceeding a limit of a personal-characteristic (which may be pain, stress, etc. (further examples are described below)) of their choosing. This can greatly increase a user's/patient's QoL. In another example, systems and methods disclosed herein can be used for elite training, for instance to improve the maximum capacity/performance for each sportsperson in any sport. Therefore, examples disclosed herein can also be used to improve physical performance.

It will be appreciated that any of the features and functionality that is described herein with respect to pain-management systems can also be implemented in a similar way for non-pain related systems.

There may be provided a computer program, which when run on a computer, causes the computer to configure any apparatus, including a circuit, controller, converter, or device disclosed herein or perform any method disclosed herein. The computer program may be a software implementation, and the computer may be considered as any appropriate hardware, including a digital signal processor, a microcontroller, and an implementation in read only memory (ROM), erasable programmable read only memory (EPROM) or electronically erasable programmable read only memory (EEPROM), as non-limiting examples. The software may be an assembly program.

The computer program may be provided on a computer readable medium, which may be a physical computer readable medium such as a disc or a memory device, or may be embodied as a transient signal. Such a transient signal may be a network download, including an internet download. There may be provided one or more non-transitory computer-readable storage media storing computer-executable instructions that, when executed by a computing system, causes the computing system to perform any method disclosed herein.

One or more embodiments will now be described by way of example only with reference to the accompanying drawings in which.

6

Figure 5:
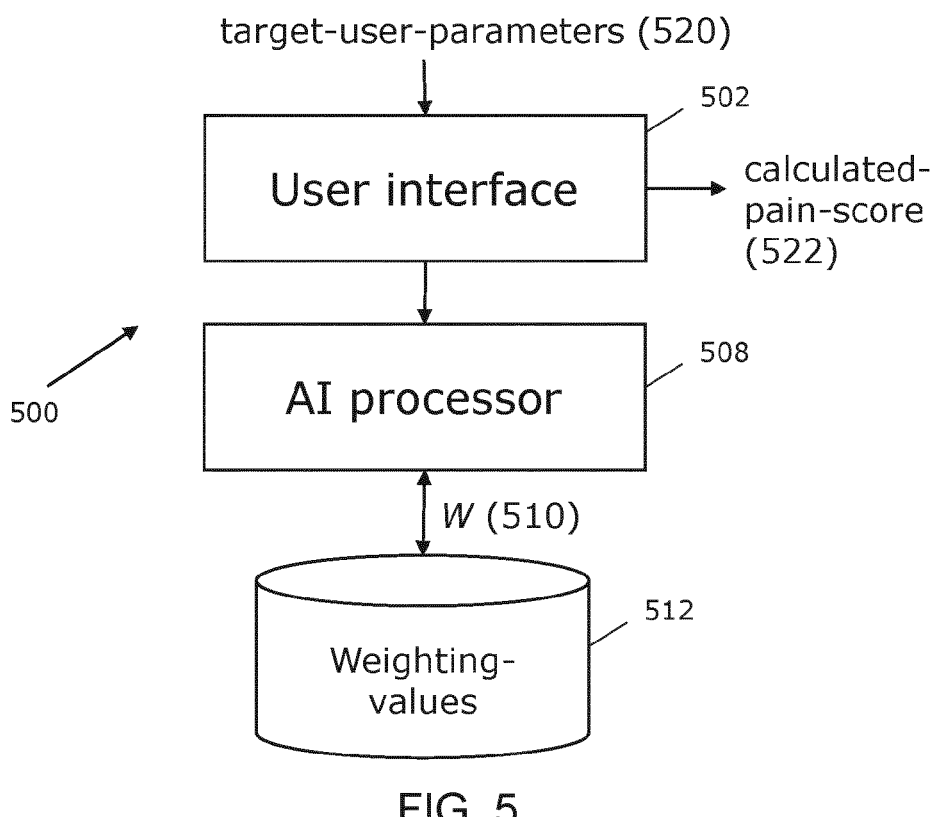
Figure 6:
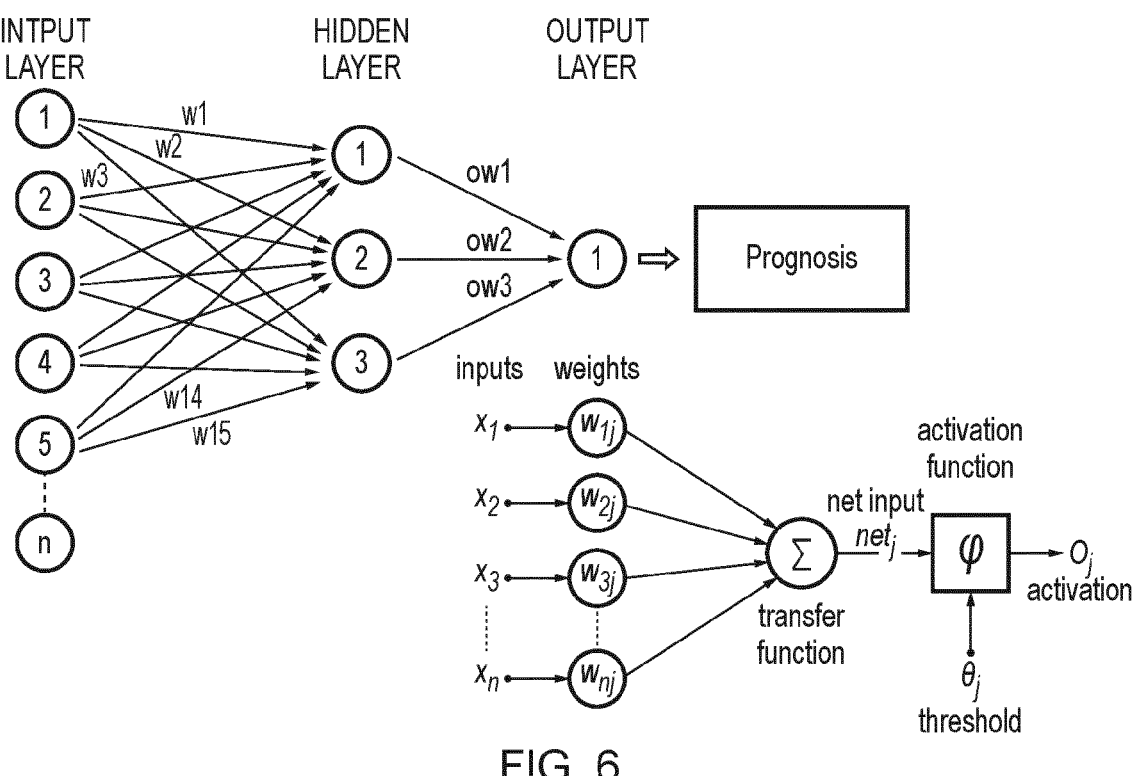
Figure 7:
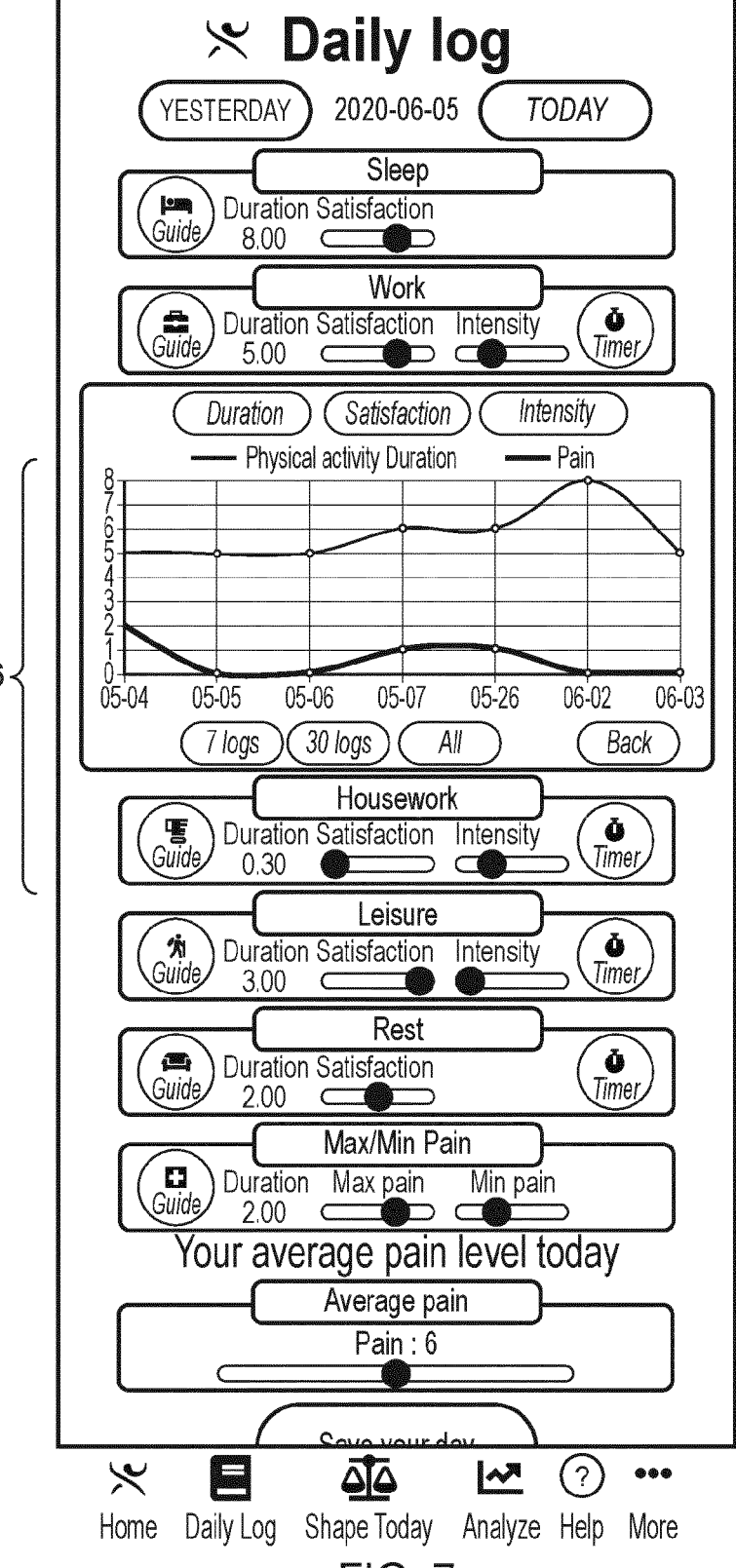
Figure 8:
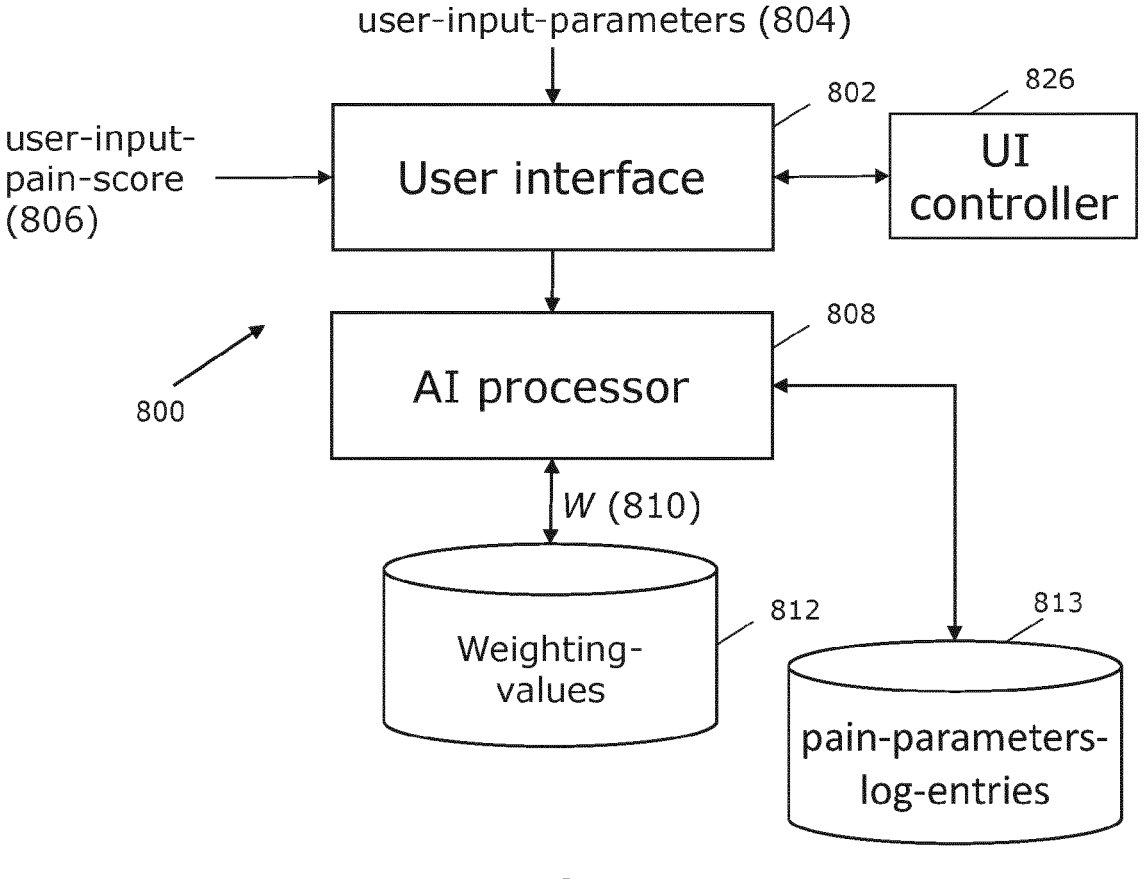
Figure 9:
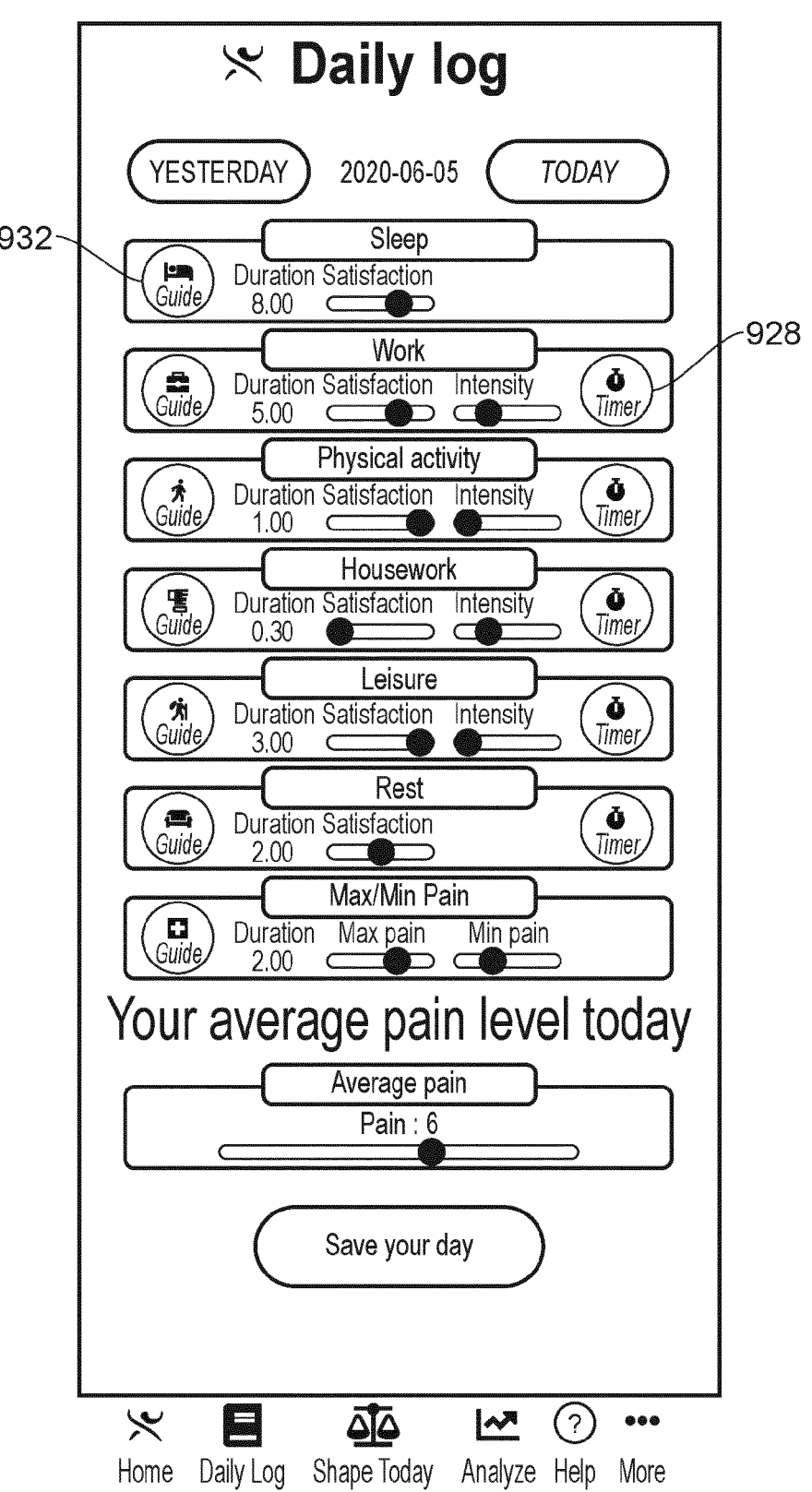
Figure 9:
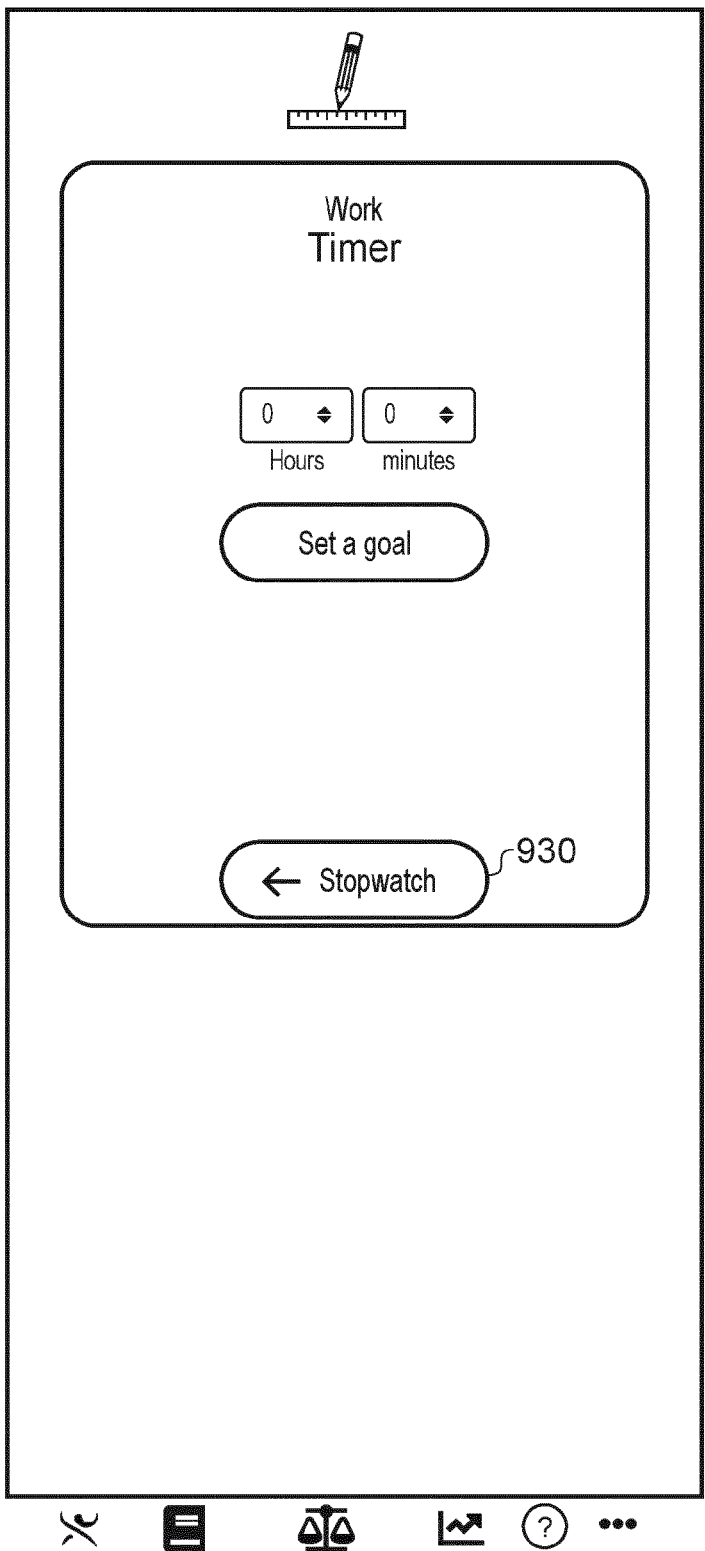
Figure 9:
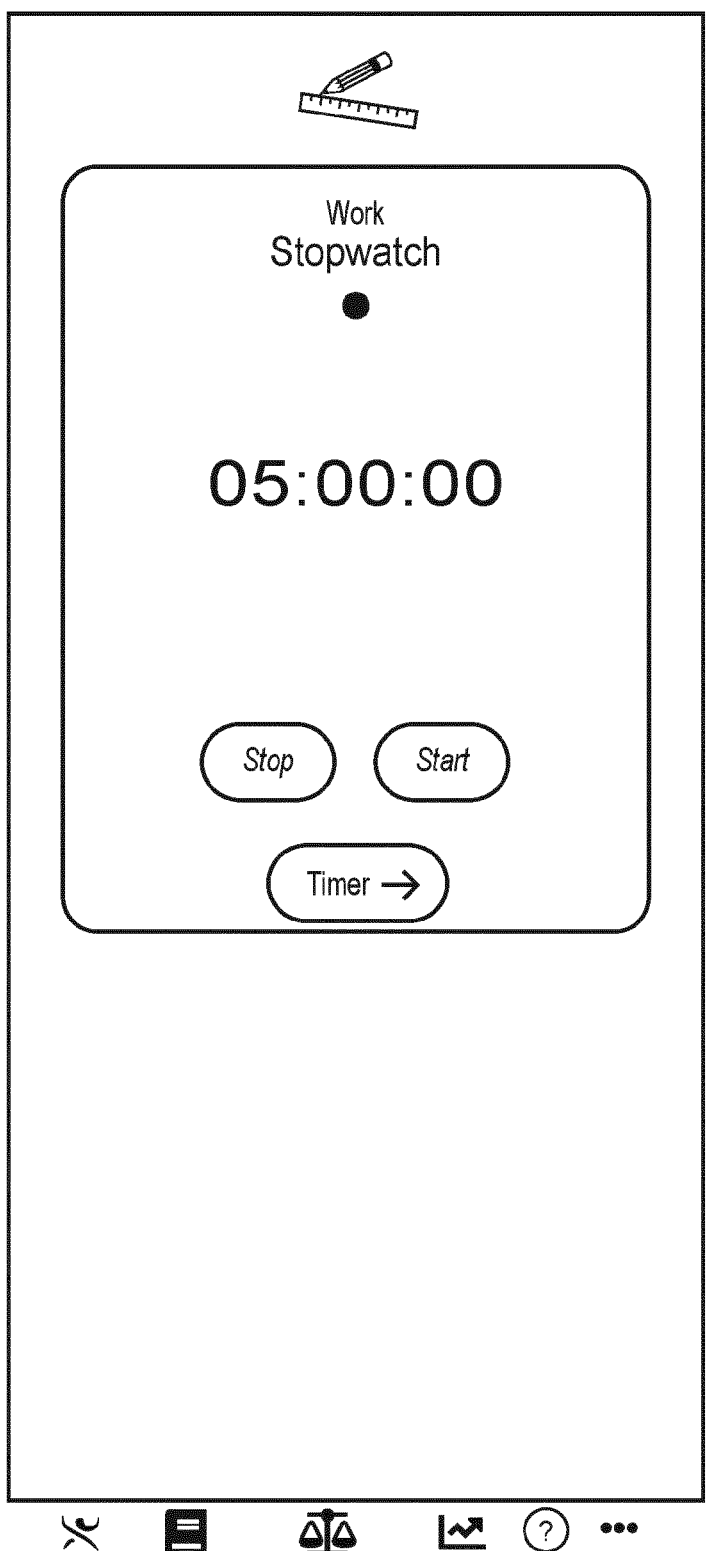
Figure 10:
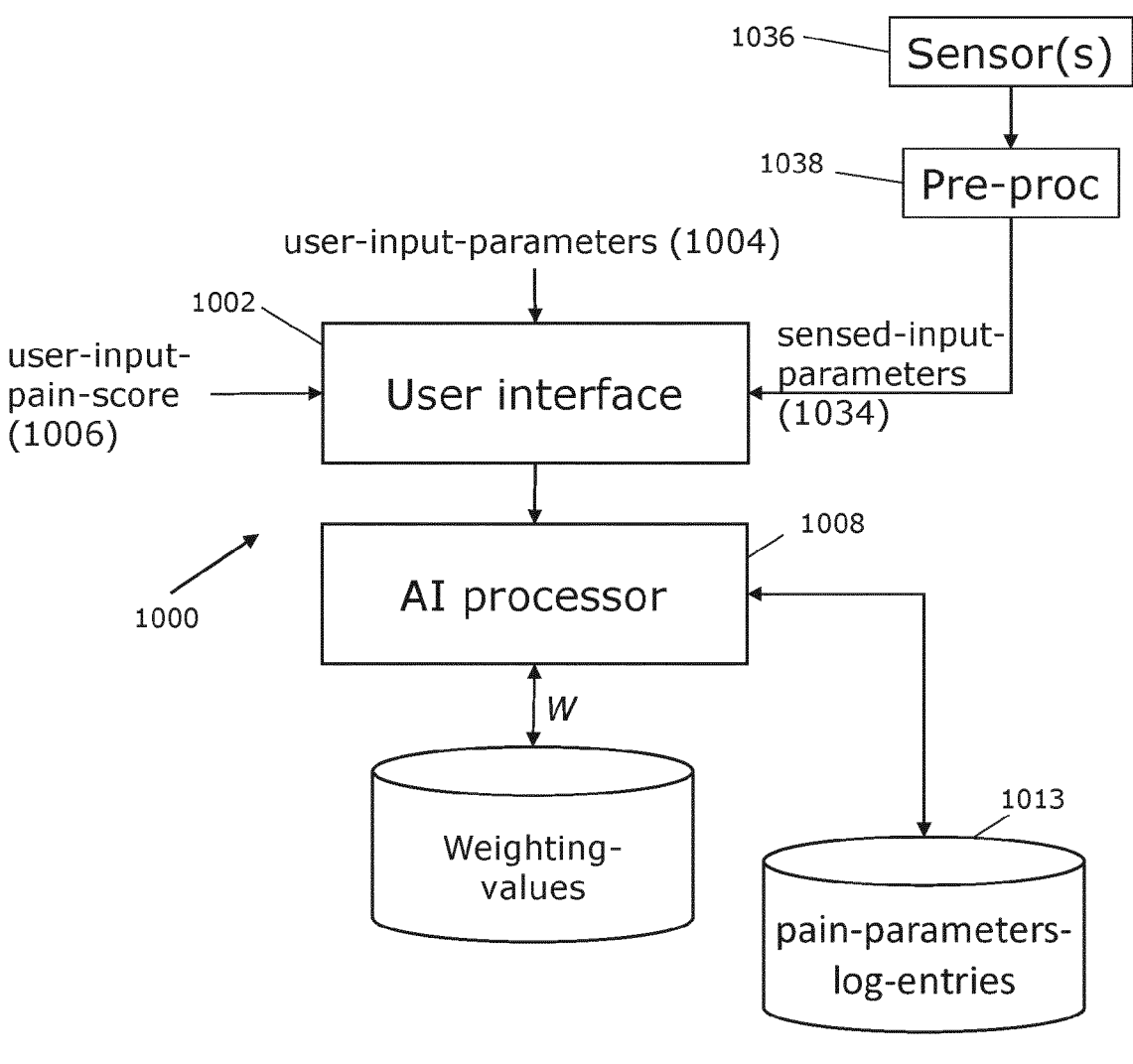
Figure 11:
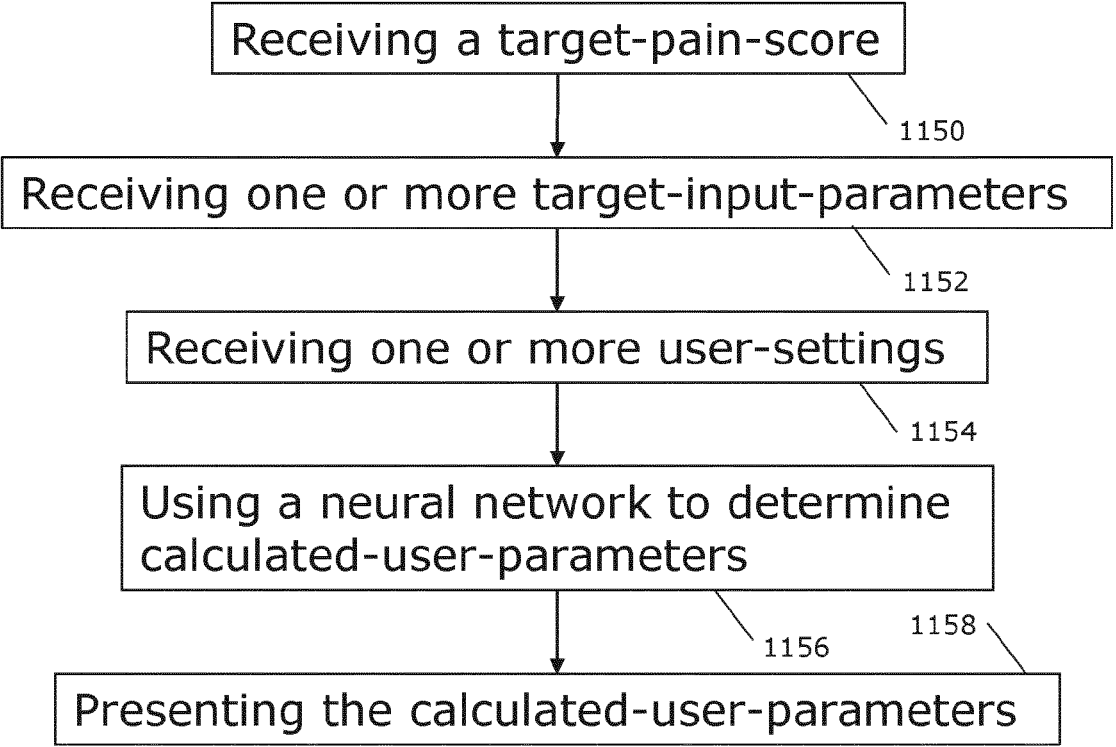

FIG. 5 shows an example embodiment of how a trained pain management system can be used to help each user predict an expected level of pain based on their planned activities;

FIG. 6 provides an overview of the functionality that can be implemented by any of the AI processors described herein;

FIG. 7 shows an example screenshot that can be displayed to each user via any of the user interfaces disclosed herein;

FIG. 8 shows another example embodiment of how a pain management system can be trained to develop an individualised pain-management model for a user;

FIG. 9 shows three example screenshots that will be used to describe examples of user-input-mechanisms;

FIG. 10 shows another example embodiment of a pain management system according to the present disclosure;

FIG. 11 shows schematically a computer-implemented method according to the present disclosure;

FIG. 12 shows the relation between responding and non-responding patients, regarding improved Pain Interference (QoL) in a clinical study;

FIG. 13 shows differences (reduction) in T-scores in Pain Interference (QoL), for responding patients in study phase one (patient 1 to 5) and phase two (patient 6 to 10) of the clinical study; and FIG. 14 shows the relation between responding and non-responding patients regarding improved Pain Intensity in the clinical study.

Chronic pain represents one of the most serious challenges to the citizens and the economy in Europe. According to the research, one in five Europeans suffers from chronic pain. Chronic pain is defined as pain that lasts for longer than 3-6 months beyond the expected period of healing. On average, people live with their chronic pain for up to 7 years. The pain affects negatively the patients' everyday life as it has a substantial impact on the daily activities. Chronic pain is also associated with psychological disorders, such as anxiety and depression. People with chronic pain are prone to drug dependency and the risk of suicide in chronic pain sufferers is at least doubled.

Many studies have found that pain is commonly overlooked and thus undertreated and sometimes not treated at all. The majority of EU countries lack specific clinical guidelines for managing chronic pain. Many patients never meet a clinician with enough knowledge about the best ways to cope with pain. The primary health care service is often the first and the only contact that the patients have in such cases-meeting a pain specialist is only available for a very fortunate few. Only 1 in 5 chronic pain patients in Europe has ever met a pain specialist and only 2% has been going through a pain management program. Other studies indicate that as low as 1% of the chronic pain patients ever meet a pain specialist for their disease. Here it is important to highlight that primary care physicians (PCPs) often don't feel competent in treatment of chronic pain. Only 50% of PCPs feel confident managing chronic pain and over half (54%) of them are not confident about what to do when a person still complains about pain. As a result of a highly limited access to pain specialists, chronic pain is improperly treated in the vast majority of cases. One of the consequences of mismanagement of pain is opiate abuse.

One or more of the embodiments disclosed herein can empower patients to manage the multidimensional aspects of chronic pain, thereby achieving much better outcomes for the patients without requiring face-to-face patient interactions.

As will be discussed in detail below, examples disclosed herein relate to an advanced self-management tool for chronic pain based on Artificial Intelligence (AI). Systems described herein can analyse data provided by each individual and, leveraging machine learning functionalities, identify pain triggers and pain protectors for the specific patient. The patient can receive concrete and actionable pieces of advice on how to mitigate the negative effects of chronic pain and improve his or her quality of life (QoL).

Figure 1:
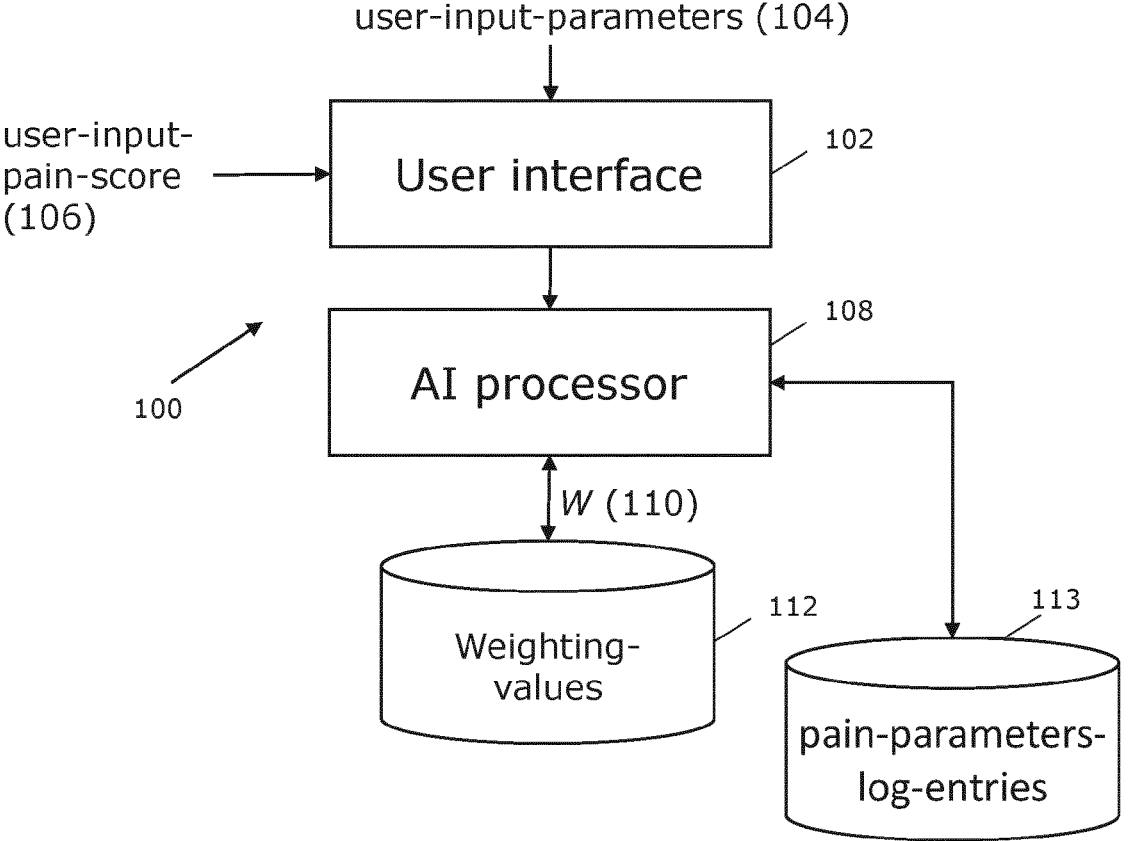
FIG. 1 shows an example embodiment of how a pain management system can be trained to develop an individualised pain-management model for each user.

FIG. 1 shows an example embodiment of how a pain management system 100 can be trained to develop an individualised pain-management model for each user, i.e. a truly patient-centric model. In this example, the pain-management model is represented by a plurality of weighting-values W 110 that are stored in a computer memory 112.

The system 100 includes a user interface 102 that receives a plurality of user-input-parameters 104. The plurality of user-input-parameters 104 represent activities and/or properties of a user during a defined period of time; more particularly, activities and/or properties that can influence the degree of chronic pain that is experienced by the user. The activities can relate to work, physical activity and leisure time, for example. The properties can relate to one or more measured or determined characteristics of the user's body such as heart rate, blood pressure, temperature, etc.

A user-input-parameter 104 can include one or more of the following characteristics, depending upon the type of parameter: (i) a duration-characteristic, which represents the duration that the user performed the activity/or exhibited the property; (ii) an intensity-characteristic, which represents the intensity with which the user performed the activity; (iii) a satisfaction-characteristic, which represents the degree of satisfaction that the user experienced when performing the activity; and (iv) a type-characteristic. Specific examples of user-input-parameters 104 that relate to activities will be described below with reference to FIG. 2. Specific examples of user-input-parameters 104 that relate to properties of the user will be described below with reference to FIG. 10.

As shown in FIG. 1 the user-interface 102 also receives a user-input pain-score 106, which represents a degree of pain experienced by the user during the same defined period of time. This can represent one or more pain values. The user-input pain-score 106 can represent the degree of pain experienced by the user that is associated with the corresponding user-input-parameters 104.

Figure 2:
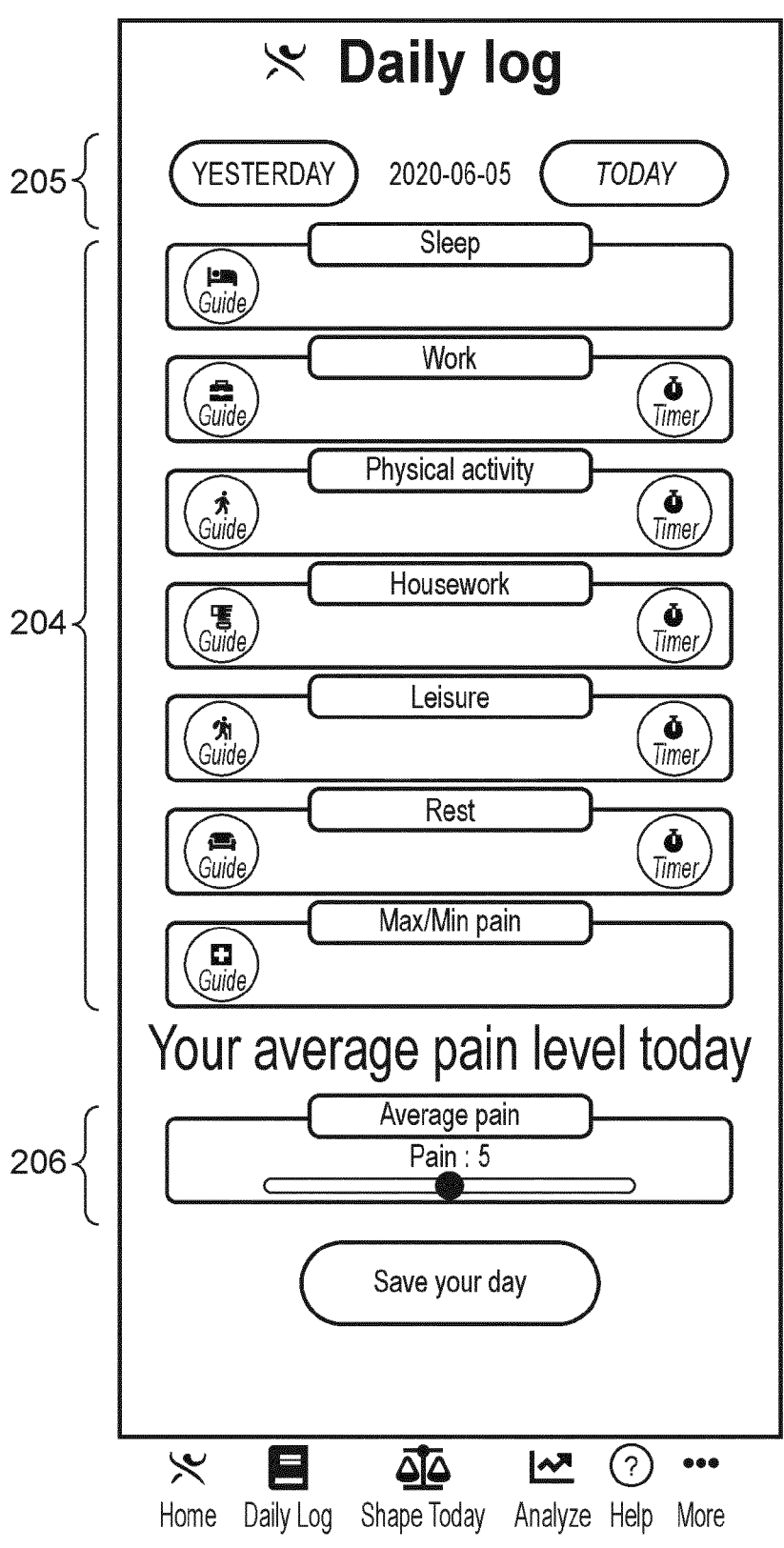
FIG. 2 shows three example screenshots that will be used to describe examples of user-input-parameters.
Figure 2:
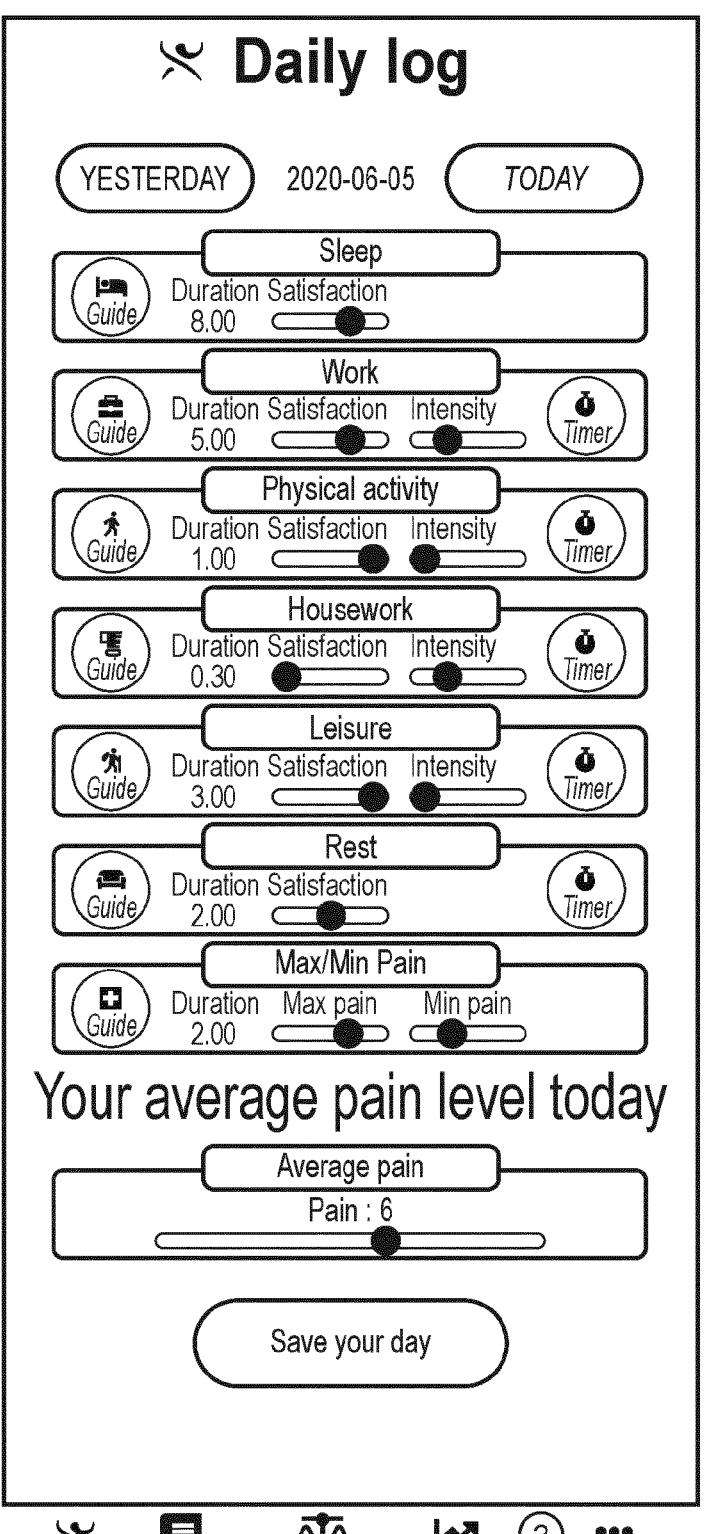
Figure 2:
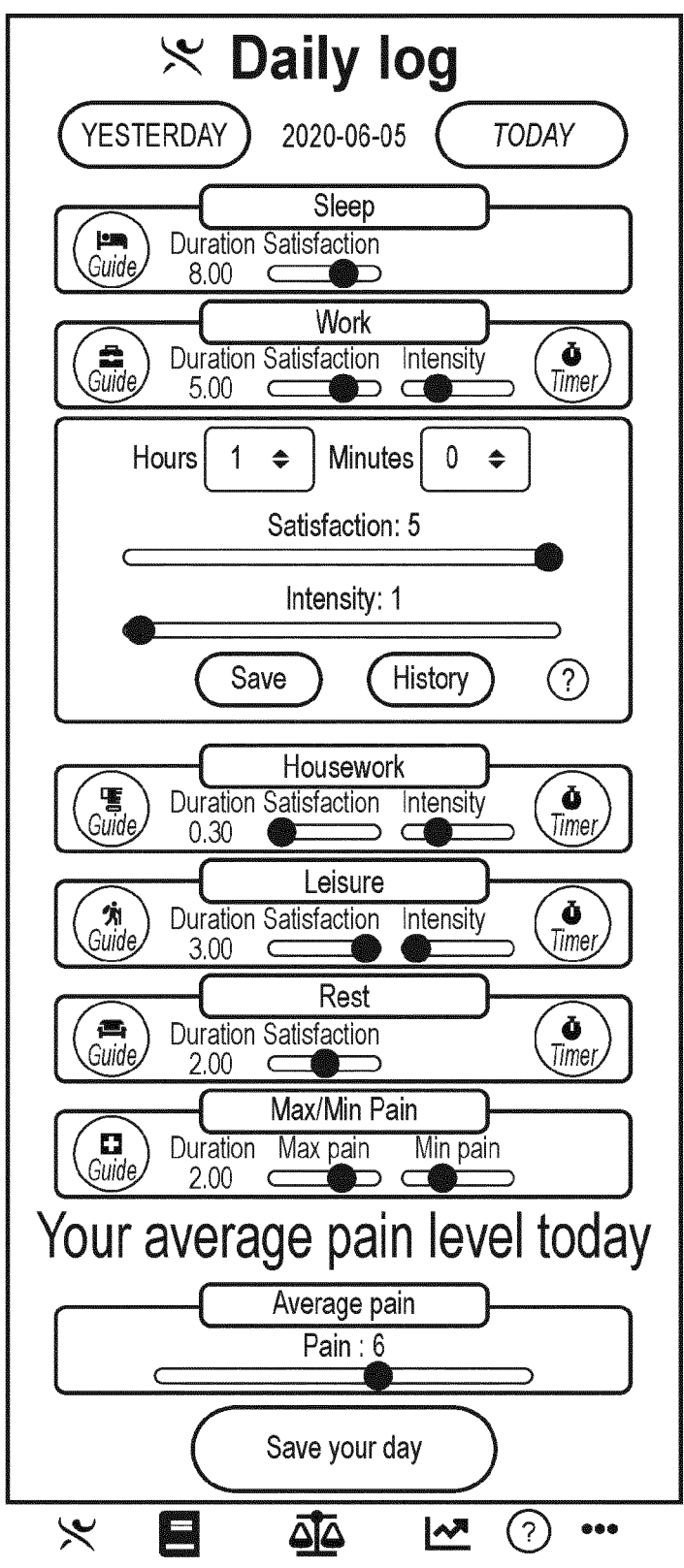

In this example, the user-input pain-score 106 represents the average pain value that the user experienced over a defined period of time (such as a day). As shown in the screenshot of FIG. 2, a user-input-parameter 104 can also relate to the user's pain, but be different to the user-input pain-score 106. In this example, again as shown in FIG. 2, the user-input-parameters 104 include (i) the maximum and minimum pain values experienced over a predetermined period of time; and (ii) the duration for which the user experienced pain (optionally the duration that the user experienced pain at a certain level).

In this example the user-input-parameters 104 represent properties/activities performed by a user over a 24-hour period, and the user-input pain-score 106 represents one or more pain values over the same 24-hour period. Optionally, each of the user-input-parameters 104 and the user-input pain-score 106 can be stored in memory with a date-identifier. The date-identifier can be associated with the corresponding user-input-parameters 104/user-input pain-score 106 when the user enters the information. For instance, the date-identifier may be provided by the user via the user interface 102 by the user selecting the date that the userinput-parameters 104 and the user-input pain-score 106 relate to. In other examples, the date-identifier may be implemented as a timestamp. Optionally the date-identifier can be attributed to the user-input-parameters 104/user-input pain-score 106 when the information is received at an AI processor 108. Use of such a date-identifier can beneficially enable the user-input-parameters 104/user-input pain-score 106 to be inspected later on as being associated with a specific date. For instance, it can be possible for plots of the user-input-parameters 104/user-input pain-score 106 to be generated to illustrate how the values have changed over time, or to perform any statistical analysis that is considered useful.

It will be appreciated from the description that follows that the user provides the user-input pain-score 106 so that the pain-management model can be trained for the individual user. Depending upon the data that is provided, the pain-management model may be sufficiently trained such that it can be used to provide useful predictions of pain (or any other output described herein) after a defined period of time, such as a few days, 8 or 9 days, or a couple of weeks. The length of time that it takes to adequately train the pain-management model can be affected by the variability in the user's daily activities-if there is a high degree of variability, then it can take longer to train the pain-management model to an acceptable level.

The user-interface 102 sends the user-input-parameters 104 to an AI processor 108. It will be appreciated that the AI processor 108 may be co-located on a device that provides the user-interface 102 to the user, or may be located remotely from a device that provides the user-interface 102. In some embodiments, the device that provides the user-interface 102 may be a user's smartphone because it is portable and readily available for the user to input the user-input-parameters 104. The functionality of the AI processor 108 may be cloud-based, such that the user-interface 102 provides the user-input-parameters 104 and the user-input pain-score 106 to the AI processor 108 over the internet. In this way a server-side application can be provided.

The AI processor 108 can implement any artificial intelligence algorithm that is known in the art, including a neural network. For example, the AI processor 108 may train an artificial neural network (ANN) using the user-input-parameters 104 as inputs, and the user-input-pain-score 106 as the ground truth (that, is the result that the ANN is intended to produce for the user-input-parameters 104 that have been provided). The AI processor 108 can apply a plurality of weighting-values W 110 (which may also be referred to as weight factors) to the plurality of user-input-parameters 104 in order to determine a calculated-pain-score, and adjust the plurality of weighting-values W 110 based on the difference between the calculated-pain-score and the user-input pain-score 106. As is known in the art, this can involve using mathematics to train an AI engine. For example, input weighting-values and output weighting-values can be iteratively calculated in epochs according to a learning rate, and then error correcting mathematics can be applied to minimize the difference between the average pain level entered by the user (the user-input-pain-score 106) and the calculated average pain level suggested by the AI engine (the calculated-pain-score). In this way, the AI processor 108 can adjust the plurality of weighting-values W 110 based on an optimization routine so that the calculated-pain-score tends towards the user-input pain-score 106 and the model is trained. More generally, the AI processor 108 can set/train a plurality of weighting-values W 110 of a neural network based on the plurality of user-input-parameters 104 and the user-input pain-score 106 for the user.

In this way, the AI processor 108 determines a plurality of weighting-values W 110 for the ANN that represent the pain-management model for the individual user. The plurality of weighting-values W 110 can be stored in computer memory 112, as shown schematically in FIG. 1, such that they can be retrieved later on for further training (during which they can be modified and saved back to memory 112), or for application to received information to generate an output for the user.

In some examples, the AI processor 108 can also store the user-input-parameters 104, the user-input pain-score 106 (and optionally the date-identifier) in a memory 113.

This memory 113 may or may not be the same as the memory 112 that stores the weighting-values W 110. This combination of the user-input-parameters 104, the user-input pain-score 106 and optionally the date-identifier may be referred to together as a pain-parameters-log-entry, and is illustrated in FIG. 2 as a "Daily log". In this example, the pain-parameters-log-entry can relate to activities that are performed, and pain that is experienced, over the period of a day. Although it will be appreciated that the period does not have to be one day—in other applications it could be 1, 2, 3 4, 6, or 12 hours, as non-limiting examples. As will also be appreciated from the following description, especially in relation to FIG. 10, the pain-parameters-log-entry can also include user-parameters that represent properties of each user in addition to, or instead of, activities that are performed by each user.

Especially in examples where the AI processor 108 is remote from the user-interface 102, the user interface 102 may also communicate a user-identifier to the AI processor 108. Such a user-identifier can be uniquely associated with an individual user's profile. In some examples the user-identifier may be stored as part of a pain-parameters-log-entry. The user interface 102 can associate the user-identifier with the corresponding user-input-parameters 104 and user-input pain-score 106 when the user interface sends this information to the AI processor 108. This can enable the AI processor 108 to use the received user-identifier to extract the correct weighting-values 110 from memory (i.e. those that are associated with the same user-identifier), such that they can be adjusted for the newly received information and the individual model for the specific user can be updated and further trained. In this way, the AI processor 108 can ensure that a model is only used for the (single) associated user, i.e. truly patient-centric, which advantageously ensures that the model is bespoke to each individual person. This has been found to be important for generating an accurate model for each user because pain can be experienced differently, and for different reasons, for each individual.

Advantageously, the pain-management model for each individual user (that can be represented by weighting-values 110) can be used to identify different pain triggers and pain protectors for the specific user.

A pain trigger can be considered as an activity (or a plurality of activities in combination) that causes the user to experience significant pain. In some examples the system 100 can determine a pain trigger by processing a plurality of pain-parameter-log-entries, where each entry represents one or more of user-input-parameters 104 and a user-input pain-score 106, at least. For instance, the system 100 can identify pain-parameter-log-entries that have a user-input pain-score 106 that is above a high-pain-trigger-threshold (such as 8 out of 10) as high-pain-parameter-log-entries. The system can then perform an analysis of the user-inputparameters 104 of the high-pain-parameter-log-entries to determine a correlation-score that represents the degree of correlation between values of corresponding user-input-parameters 104 in the high-pain-parameter-log-entries. The analysis can be statistical analysis, machine learning analysis, or any other type of analysis that can determine a degree of correlation between values of corresponding user-input-parameters 104 in the high-pain-parameter-log-entries. For example, the system 100 can identify one or more user-parameters as pain triggers if they have a correlation-score that satisfies a correlation-criterion. Examples of such a correlation-criterion include: a correlation-score that is above a correlation-threshold; the highest correlation-score for all of the user-parameters; and a predetermined number of the highest correlation-scores for all of the user-parameters (e.g. the 3 user-parameters that have the highest correlation-scores). The system can then display the pain triggers to the user (for example using the user interface 102). In this way, the system 100 can beneficially determine and display certain user-input-parameters, and their associated values, to a user as a "pain trigger" such that each user can modify their behaviour to avoid those pain triggers and thereby reduce their level of pain in the future.

A pain protector can be considered as an activity (or a plurality of activities in combination) that results in the user experiencing a low amount of pain. In some examples the system 100 can determine a pain protector by processing a plurality of pain-parameter-log-entries, where each entry represents one or more of user-input-parameters 104 and a user-input pain-score 106, at least. For instance, the system 100 can identify pain-parameter-log-entries that have a user-input pain-score 106 that is below a low-pain-trigger-threshold (such as 3 out of 10) as low-pain-parameter-log-entries. The system can then perform an analysis of the user-input-parameters 104 of the low-pain-parameter-log-entries to determine correlation-scores and subsequently identify specific user-parameters as pain protectors in a similar way to that described above for pain triggers. Again, such analysis can be statistical analysis, machine learning analysis, or any other type of analysis. As above, in this way, the system 100 can beneficially determine and present certain user-input-parameters, and their associated values, to a user as a "pain protector".

In this way, the pain-management model can be used to teach each individual how to become more active by learning their pain triggers and pain protectors. The human brain can handle only up to four variables rationally at any point in time. An AI engine, provided by the AI processor 108, can be harnessed to process many more, multi-variable functional aspects of each individual's pain level. This can allow each chronic pain patient a unique ability for self-management and to take an active role of their condition, which directly translates into a better QoL.

FIG. 2 shows three example screenshots that will be used to describe examples of user-input-parameters 204 and a user-input-pain-score 206, and how they can be provided by a user via a graphical user interface (GUI) to train a pain-management-model for an individual user. A GUI is one example of the user-interface of FIG. 1.

The first screenshot shows the GUI before a user has entered any activity or pain information. As shown in FIG. 2, the user-input-parameters 204 in this example are the following:

a sleep-parameter;
a work-parameter;
a physical-activity-parameter;
a housework-parameter;

a leisure-parameter;

a rest-parameter; and a pain-range-parameter.

It will be appreciated that any other parameters can also or alternatively be used, and in some examples can be configured by the user. The value for one or more of the parameters described herein, including a stress level parameter for instance, can be determined by processing answers that the user has provided in a questionnaire. The value of a stress level parameter can have a significant effect on a user's pain.

It will also be appreciated that since the user-input-parameters 204 will be used to generate an individualised pain-management model, it does not matter if different users score the user-input-parameters 204 differently; as long as the user scores the user-input-parameters 204 in a consistent way, then the pain-management model will be appropriately trained for that user. Therefore, beneficially, the user does not have to worry about scoring their activities against a standard scoring scheme that is determined by someone else. Furthermore, each user/patient will have their own AI engine trained exclusively on their own data.

In this example, the user-input-pain-score 206 is the average pain experienced by the user in the day.

The first screenshot also shows one way in which the user can provide the date 205 with which the user-input-parameters 204 and the user-input-pain-score 206 are associated. As discussed above, the user interface can determine a date-identifier based on the date 205 that the user provides.

The second screenshot in FIG. 2 shows examples of information that the user has provided for the user-input-parameters, and the corresponding characteristics. More particularly, as non-limiting examples:

for the sleep-parameter: a duration-characteristic and a satisfaction-characteristic (in this example on a sliding scale between a minimum and a maximum value, such between 1 and 5);

for the work-parameter: a duration-characteristic, a satisfaction-characteristic and an intensity-characteristic (in this example on a sliding scale between a minimum and a maximum value);

for the physical-activity-parameter: a duration-characteristic, a satisfaction-characteristic and an intensity-characteristic;

for the housework-parameter: a duration-characteristic, a satisfaction-characteristic and an intensity-characteristic;

for the leisure-parameter: a duration-characteristic, a satisfaction-characteristic and an intensity-characteristic;

for the rest-parameter: a duration-characteristic and a satisfaction-characteristic; and for the pain-range-parameter: a maximum-pain-characteristic, a minimum-pain-characteristic and a duration-characteristic.

Although not shown in this example, one or more of the input-parameters may also have a type-characteristic that identifies a specific type of activity. For instance, the physical-activity-parameter may have a type-characteristic that can represent different types of physical activity, such as cycling, running, swimming, etc.

In this example, each duration-characteristic corresponds to an amount of time spent performing the activity (or experiencing pain for the pain-range-parameter) during a single day.

As will be discussed below, in some examples one or more of the characteristics for a parameter may be automatically provided by associated software. For instance, software is known in the art that can automatically classify parameters such as sleep, rest and physical activity from signals that are available from wearable sensors. Such known software can also determine associated duration-characteristics.

The third screenshot shows in more detail how a user can provide input for the specific characteristics of the work-parameter.

It has been found that after a short training period, the pain-management model can be adequately trained such that it is competent to make suggestions on how a user can plan their day, for example to achieve the maximum level of function at the lowest possible level of pain. The use of the AI processor can enable multiple types of data to be collected and analysed such that multifaceted causal aspects of the individual's chronic pain can be determined.

Figure 3:
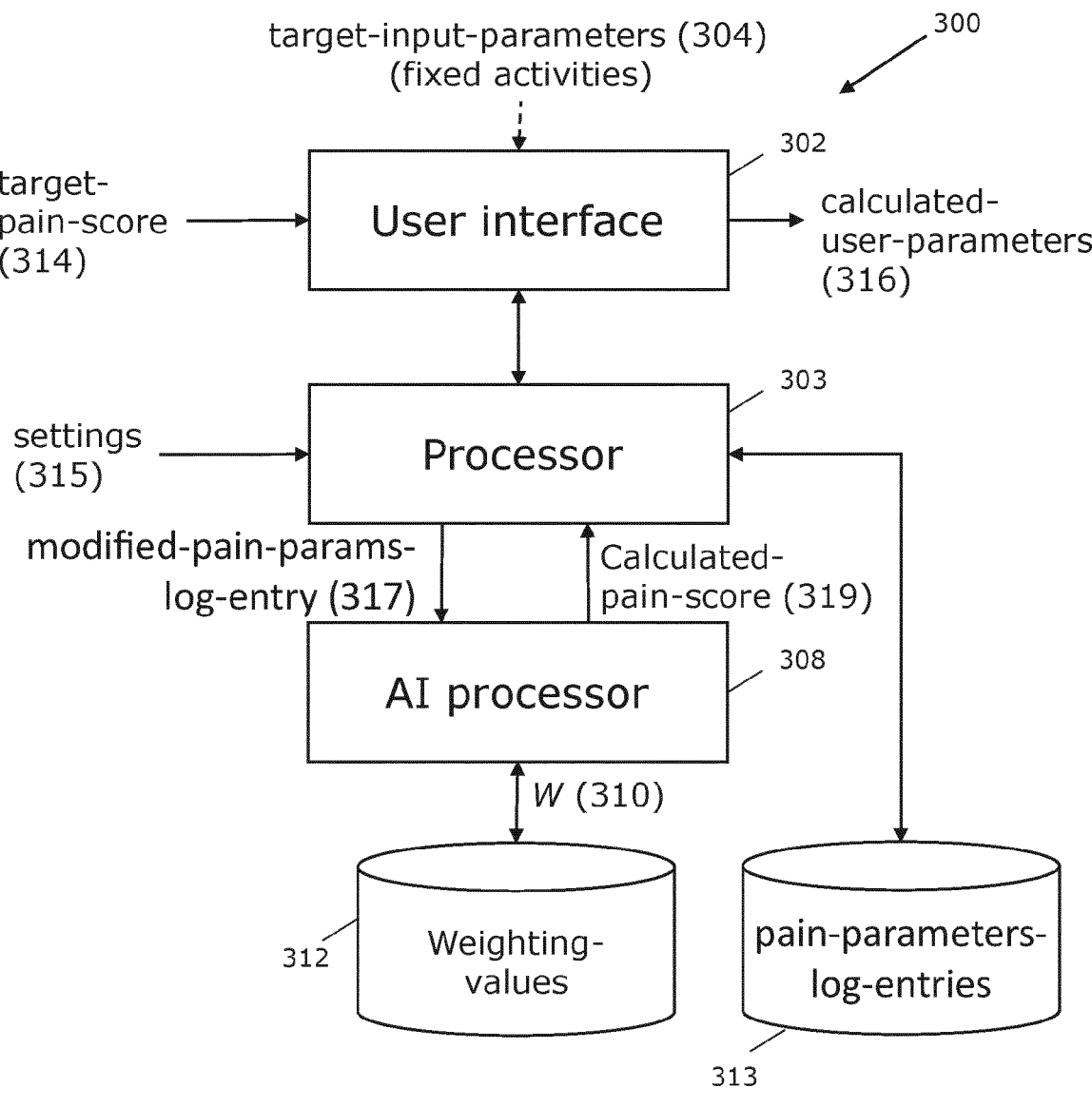
FIG. 3 shows an example embodiment of how a trained pain management system can be used to help each user achieve a desired level of pain in a day.

FIG. 3 shows an example embodiment of how a trained pain management system 300 can be used to help the user achieve a desired level of pain in a day. Features of FIG. 3 that are also shown in FIG. 1 will be given corresponding reference numbers in the 300 series, and will not necessarily be described in detail again here.

In this example, the user provides a target-pain-score 314 to the user-interface 302. The target-pain-score 314 represents a level of pain that the user considers acceptable when performing a variety of activities during a defined period of time. In some examples, the user can also provide one or more target-input-parameters 304 (which may be referred to as fixed activities), which typically will be a subset of the full list of input-parameters that are available. As will be discussed below, the system 300 can then provide one or more calculated-user-parameters 316 based on the target-pain-score 314 and the target-input-parameters 304. The calculated-user-parameters 316 can represent suggestions for values for one or more of the input-parameters (that are not provided as an input by the user) that are expected to achieve the target-pain-score 314.

In this example, the user-interface 302 sends the target-pain-score 314 and the entered target-input-parameters 304 to a processor 303 that will perform some processing on the target-pain-score 314 and the entered target-input-parameters 304 before using the pain-management model. As will be discussed in detail below.

In addition to receiving the target-pain-score 314 and the entered target-input-parameters 304 from the user interface 302, the processor 303 in this implementation also receives one or more settings 315. The settings 315 may represent one or more types of input-parameter (activity) that are to be increased or decreased. The settings 315 may for example include user-settings, default-settings, or physician-settings as discussed in more detail below.

User-settings can represent one or more types of input-parameter (activity) that the user has indicated are to be increased or decreased. The user-settings 315 may be received directly from the user interface 302, or they may be retrieved from a computer memory that stores a user profile. The user-settings may represent one or more types of input-parameter (activity) that the user is looking to increase or decrease. This can be a type of input-parameter that is expected to provide a health benefit to each user, which may be an activity that is important to them. For this specific example, we will assume that the user-setting represents a desire to increase the duration of the physical-activity-parameter. Although it will be appreciated that the user-setting 315 can represent a preference for increasing or decreasing any input-parameter.

In some examples the user-settings can represent one or more types of input-parameter (activity) that the system 300 has determined should be increased or decreased. For example, the system may determine user-settings based on one or more pieces of information in a user's profile. In one implementation, the system 300 can process one or more pain-location-settings that the user has included in their profile to determine appropriate user-settings. This can include, as a non-limiting example, determining a user-setting to increase a duration-characteristic for a rest-parameter if a pain-location-setting indicates lower back pain. Such a determination can be performed by the system 300 according to any suitable algorithm or accessing any database/look-up table that is associated with the system 300.

Default-settings can also represent one or more types of input-parameter (activity) that are to be increased or decreased, but are not necessarily user defined. This can include an indication that all types of input-parameter are equally important and therefore should be increased or decreased equally. That is, in some examples the settings 315 may indicate that all of the input-parameters are to be increased or decreased at the same rate.

Physician-settings can represent one or more types of input-parameter (activity) that a physician has indicated are to be increased or decreased. Advantageously the physician can therefore provide information such that the user can change their behaviours in a way that the physician has identified as likely to improve their quality of life.

The processor 303 initially inspects a set of historic pain-parameter-log-entries (daily logs) that are stored in memory 313 associated with the same user, to identify the pain-parameters-log-entry that is a match with the received target-pain-score 314 and the entered target-input-parameters 304. For instance, the processor 303 may determine a degree of correlation between (i) the received target-pain-score 314 and the entered target-input-parameters 304; and (ii) each of the pain-parameter-log-entries that are stored in memory 313. The processor 303 may then select the pain-parameters-log-entry that has the highest correlation as a matched-pain-parameters-log-entry, or at least one that has a sufficiently high correlation such that it is expected to provide a reasonable starting point for the subsequent processing.

As a next step, the processor 303 can modify the matched-pain-parameters-log-entry based on the settings 315. This can involve increasing or decreasing one or more user-input-parameters of the matched-pain-parameters-log-entry. For this example, where the settings 315 represent a desire to increase the duration of the physical-activity-parameter, the processor 303 will increase the duration-characteristic of the physical-activity-parameter in the matched-pain-parameters-log-entry. The processor 303 may temporarily save this modified entry as a modified-pain-parameters-log-entry. In some examples the processor 303 can increase the duration-characteristic by a predefined amount that may be coded (e.g. hard-coded) into the software, or may be provided as part of the settings 315. For instance, the predetermined amount may be a predetermined period of time or may be a predetermined percentage increase. Optionally, the processor 303 may include the original target-input-parameters 304 in the modified-pain-parameters-log-entry without amendment. That is, the processor 303 can prevent the original target-input-parameters 304 from being modified (at least initially) on the basis that the user has indicated that these input-parameters are fixed.

The processor 303 then sends the full set of input-parameters of the modified-pain-parameters-log-entry 317 to the AI processor 308. The AI processor 308 applies a neural network using each user's individual pain-management-model (as defined by the weighting-values 310 stored in memory 312) to the modified-pain-parameters-log-entry 317 in order to determine a calculated-pain-score 319. In this way, the system uses a neural network that has been trained for the individual user to determine one or more calculated-user-parameters 316 based on the target-pain-score 314 and the target-input-parameters 304, wherein at least one of the calculated-user-parameters 316 is set based on the user-settings 315. The AI processor 308 then sends the calculated-pain-score 319 back to the processor 303. In some examples, the user interface 302 can then present the one or more calculated-user-parameters 316 (and optionally the calculated-pain-score 319) to each user.

In this example, the processor 303 compares the calculated-pain-score 319 to the target-pain-score 314. If the calculated-pain-score 319 is greater than the target-pain-score 314, then the modified-pain-parameters-log-entry 317 may be considered unacceptable because it results in too much pain for the user. (It will be appreciated that the calculated-pain-score 319 may be greater than the target-pain-score 314 because the duration of physical activity has been increased in this example.) If this is the case, the processor 303 can adjust one or more of the input-parameters (for instance not one that relates to the target-input-parameters 304 or the physical-activity-parameter that is identified by the settings 315) of the modified-pain-parameters-log-entry 317. For instance, the processor 303 may increase the duration-characteristic of the rest-parameter or decrease the intensity-characteristic of the work-parameter, as non-limiting examples. The processor 303 can adjust the one or more other input-parameters based on a predetermined set of rules, which may or may not be provided as part of the user-settings 315 to indicate which activities are less important to the user.

The processor 303 then sends the full set of revised input-parameters of the modified-pain-parameters-log-entry 317 to the AI processor 308. The AI processor 308 applies a neural network using the user's individual pain-management-model (as defined by the weighting-values 310 stored in memory 312) to the adjusted modified-pain-parameters-log-entry 317 in order to determine a revised calculated-pain-score 319. The processor 303 compares the revised calculated-pain-score 319 to the target-pain-score 314, and will continue around the loop of adjusting the one or more other input-parameters and revising the calculated-pain-score 319 until the calculated-pain-score 319 is less than or equal to the target-pain-score 314, or until a predetermined number of iterations have been performed. Once either of these requirements is satisfied, the processor 330 sends the last iteration of the modified-pain-parameters-log-entry 317 to the user interface 302 such that it can display the calculated-user-parameters 316 to the user. If the processor 303 performs the predetermined number of iterations without achieving the target-pain-score 314, then the processor 303 can instruct the user interface 302 to display an appropriate message to the user, such as: "Unable to identify a combination of activities without exceeding the target pain level". In this way, the processor 303 can repeat the compare step one or more times for the adjusted calculated-pain-score, in some applications a plurality of times up to a predetermined maximum number.

Assuming that the predetermined number of iterations is not reached, the calculated-user-parameters 316 represent a set of activities that the user should be able to perform without exceeding their target-pain-score 314, while increasing or decreasing one of the user-parameters in line with the settings 315. In this way, the system can advantageously guide the user to change their behaviours in a way that improves their health and wellbeing with a reduced likelihood of exceeding a pain limit of their choosing. This can greatly increase a user's/patient's quality of life (QoL). Beneficially, the system 300 can try to increase the activities of choice that the user has indicated in the settings as being of high value to the user, until the set pain threshold is reached. Furthermore, it may not be possible for a patient/ user to be able to recognise what changes can to be made to their behaviours without a system disclosed herein because there can be too many variables for the human brain to be able to compute to identify correlations between activities undertaken and the associated pain. The systems described herein can be used to improve the QoL of patients/user irrespective of a sub-optimal current activity balance, e.g. whether they are over-active or under-active in their daily activities. This can be achieved through use of appropriate settings 315. It will be appreciated that a user can be over-active or under-active in relation to specific activities. For instance, a person that is afraid to move can be considered as over-active in their amount of rest during a day, and a person that refuses to accept a permanent injury and continues as before can be considered as over-active in physical activity, work, etc. but under-active in rest. In some implementations, the pain-management model can be used to calculate the optimal exercise time and intensity for every single patient. Systems described herein can guide the user to find the right activity balance, e.g. balance between activity time and rest time for that specific user.

In some examples, the processor 303 can compare the value of each input-parameter in the modified-pain-parameters-log-entry 317 with the pain-parameters-log-entries stored in memory 313. If the processor 303 determines that the value of an input-parameter in the modified-pain-parameters-log-entry 317 is outside of a range of the corresponding input-parameters in the pain-parameters-log-entries, then the processor can cause an error message to be displayed to the user. Such an error message may be "You are asking for values the AI engine is not trained on. You have not performed such activities before!". Also, the processor 303 may not pass the modified-pain-parameters-log-entry 317 to the AI processor 308 for determining the calculated-pain-score 319. This is on the basis that the resultant calculated-pain-score 319 may not be reliable because the AI engine has not been trained on such values.

Figure 4:
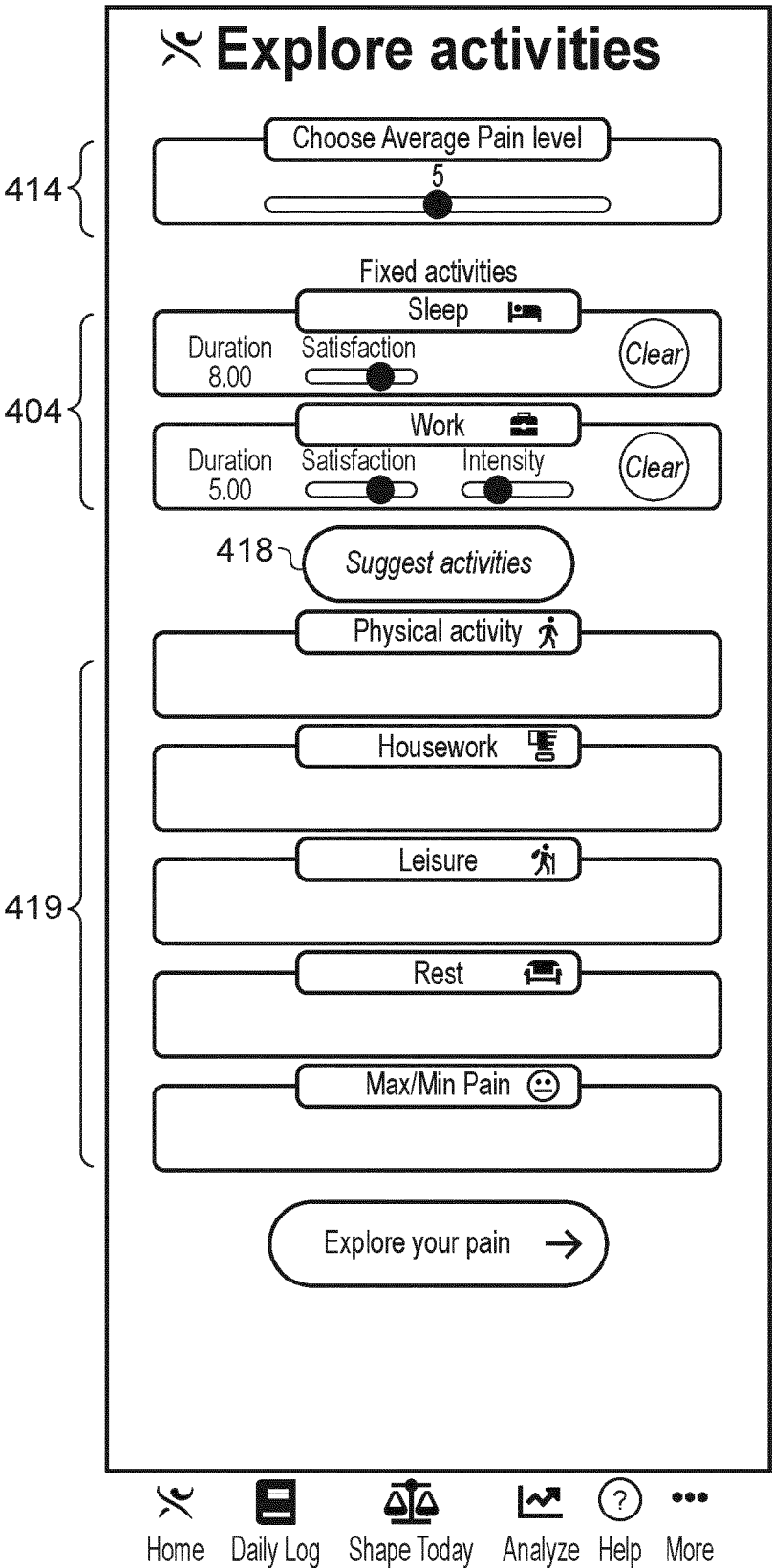
FIG. 4 shows example screenshots that will be used to describe how the user-interface of FIG. 3 can be used to provide each user with calculated-user-parameters.
Figure 4:
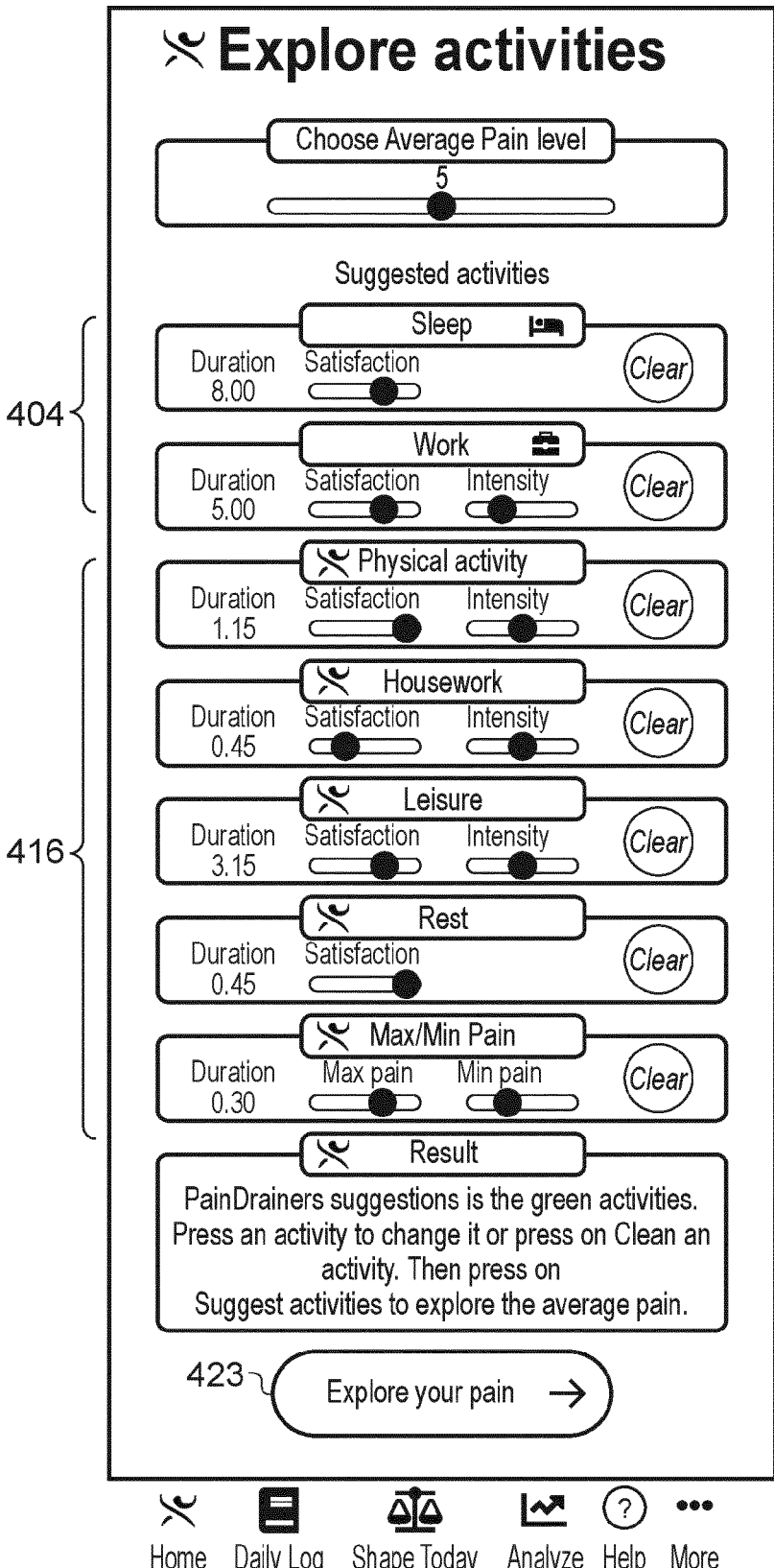
Figure 4:
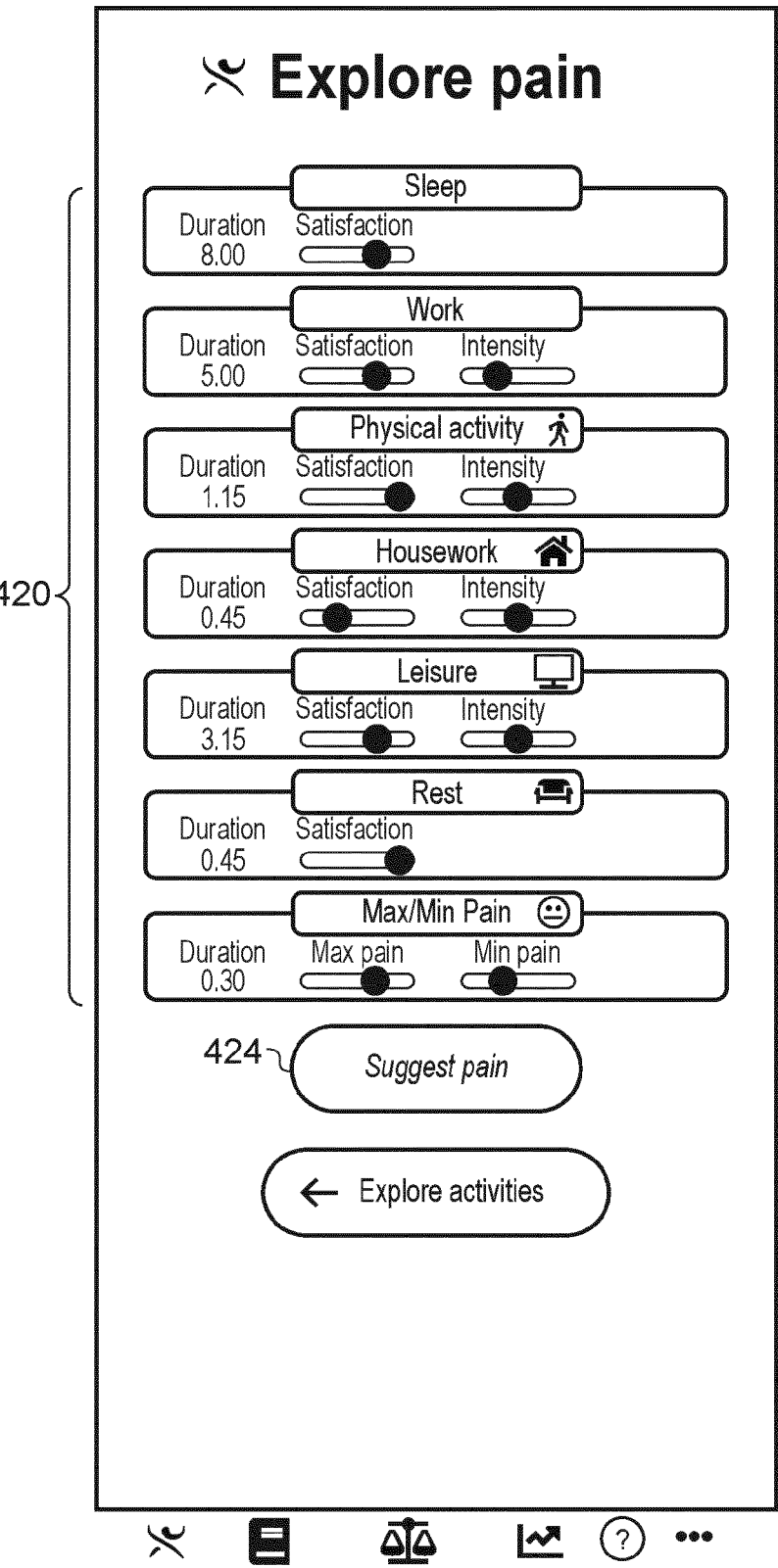
Figure 4:
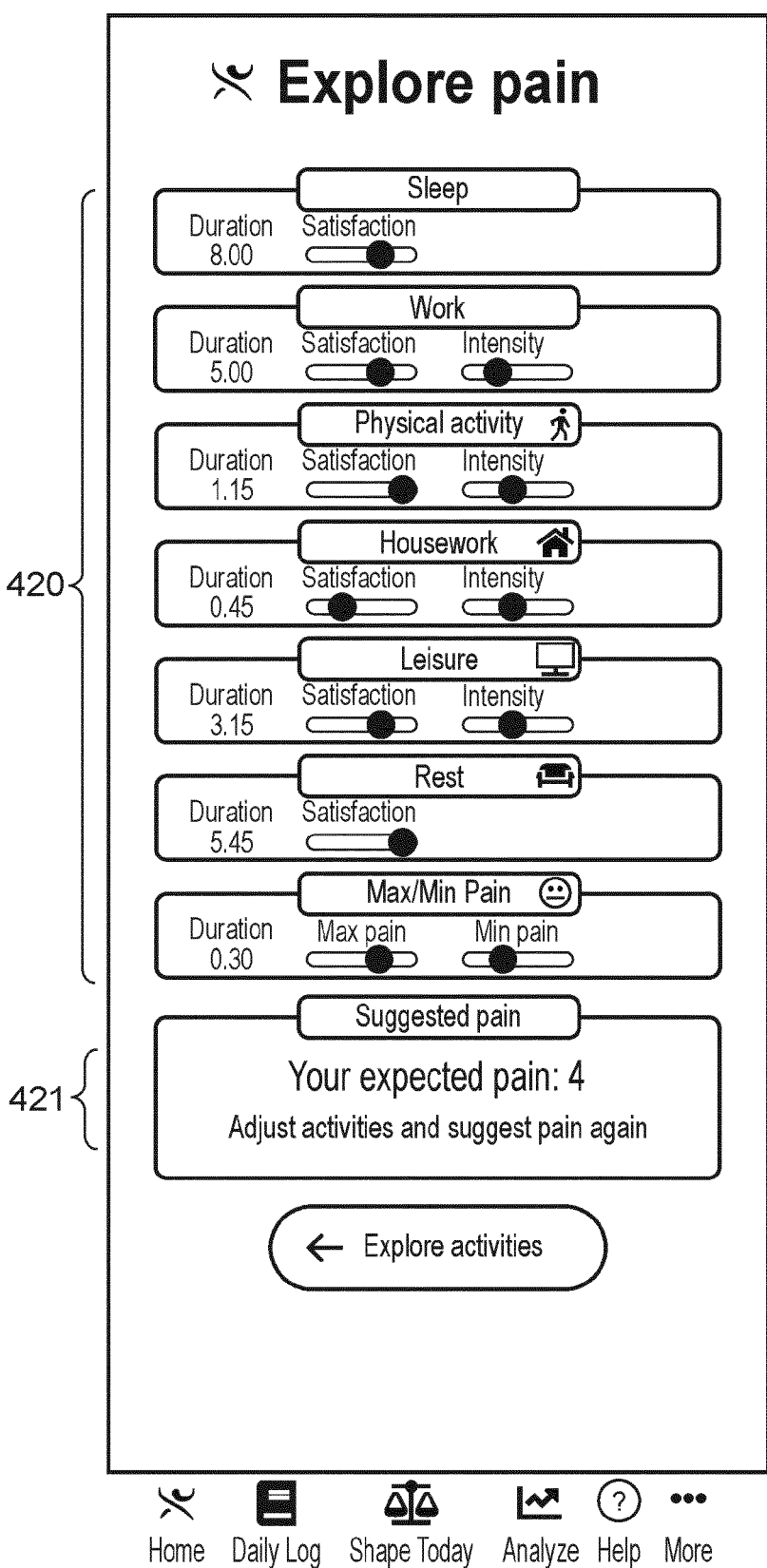

FIG. 4 shows example screenshots that will be used to describe how the user-interface of FIG. 3 can be used to provide the user with calculated-user-parameters 416.

With reference to the first screenshot, the user can provide the target-pain-score 414 as an average pain level in this example, using a slider. The user has also provided information for two of the input-parameters in this implementation, which results in them being considered as target-input-parameters 404. The target-input-parameters 404 in the first screenshot of FIG. 4 are: a sleep-parameter and a work-parameter. These target-input-parameters 404 can be referred to as fixed activities. The user could also, or instead, provide information for any of the other input-parameters 419, in which case the system would move them to the list of fixed activities and they would be processed as target-input-parameters. In this way, any activities (input-parameters) for which the user has provided input will be considered as fixed activities.

Once the user is satisfied with the information that they have entered, they can cause the system to calculate and display the calculated-user-parameters 416. In this example by selecting a "Suggest activities" button 418. The system will perform the processing that is described in detail with reference to FIG. 3 such that it displays calculated-user-parameters 416 to the user, as shown in the second screenshot.

As also shown in the second screenshot, in this example the user is provided with an "Explore your pain" button 423, which they can press to explore how modifying one or more of the input-parameters would affect their expected level of pain. Optionally, the user can modify one or more of the calculated-user-parameters 416 (and in some examples also modify one or more of the target-input-parameters 404) before they press the "Explore your pain" button 423. For instance, the user can interact with the duration values or the sliders that are shown in the second screenshot to adjust a characteristic associated with one or more of the input-parameters.

After the user selects the "Explore your pain" button 423, they will be presented with the third screenshot. Using this screenshot, they can adjust the levels of any of the input-parameters 420 (here both the calculated-user-parameters and the target-input-parameters). Once the user has adjusted the input-parameters 420, they can select the "Suggest pain" button 424 to determine a new calculated-pain-score. The fourth screenshot of FIG. 4 shows the calculated-pain-score 421 along with the associated input-parameters 420. In this example, the user has increased the duration of rest from 0.45 hours to 5.45 hours, which has caused their expected level of pain to reduce to a level of 4 (shown as the calculated-pain-score 421) from a level of 5 (shown as the target-pain-score 414).

In this way, the system can present to the user, via the user interface, an option (the "Explore activities" button 423) for modifying one or more of the calculated-user-parameters 416. Once the system receives one or more modified calculated-user-parameters from the user interface (that are representative of user input), it can apply a neural network that has been trained for the individual user to the modified calculated-user-parameters to determine a modified calculated-pain-score and present the modified calculated-pain-score using the user interface. Advantageously this can provide the user with the functionality to fine tune the proposed set of daily activities to better suit their needs, while still not expecting to exceed their target-pain-score.

In some examples, the system can automatically determine and present calculated-user-parameters 416 to the user in response to one or more predefined triggers. For instance, as soon as the user enters information for a sleep-parameter (which can be expected to be shortly after the user wakes up in the morning), the system may determine and present calculated-user-parameters 416 in accordance with one or more settings (as discussed above). In this way, the system can proactively propose a daily log for the user that is intended to change their behaviours in line with the one or more settings.

FIG. 5 shows an example embodiment of how a trained pain management system 500 can be used to help the user predict an expected level of pain based on their planned activities. Features of FIG. 5 that are also shown in either FIG. 1 or FIG. 3 will be given corresponding reference numbers in the 500 series, and will not necessarily be described in detail again here.

In this example, the user provides target-user-parameters 520 to the user-interface 502. The target-user-parameters 520 represents a set of activities that the user would like to perform in a day, and for which they would like a prediction of their expected level of pain.

The system 500 can then provide a calculated-pain-score 522 based on the target-user-parameters 520. This can be achieved by the user-interface 502 sending the target-user-parameters 520 to the AI processor 508. The AI processor 508 then applies the weighting-values W 510 to the target-user-parameters 520 to determine the calculated-pain-score 522.

It will be appreciated that the functionality described with reference to FIG. 5 is similar to part of the functionality that is described with reference to FIG. 4, in that it provides the user with the opportunity to modify the target-user-parameters 520 to see how the modifications affect the calculated-pain-score 522. The user can therefore plan a day that achieves an appropriate balance between being able to perform the activities that they wish to, while reducing the likelihood that they will exceed what they have set as a maximum level of pain.

FIG. 6 provides an overview of the functionality that can be implemented by any of the AI processors described herein. FIG. 6 schematically illustrates a neural network that has an input layer, one hidden layer in this example (although it will be appreciated that there could be any number of hidden layers) and an output-layer. The output layer can provide a prognosis (in this example a calculated-pain-score).

FIG. 7 shows an example screenshot that can be displayed to a user via any of the user interfaces disclosed herein. FIG. 7 shows how the work-parameter 726 can be expanded by a user to show historic information for that parameter along with the associated pain-score. This historic information can be provided to the user interface from a memory that stores pain-parameter-log-entries, such as the memory that is shown in FIG. 1. In this way, the user can browse the stored historic information to look for correlations between specific activities and increases or decreases in pain.

FIG. 8 shows another example embodiment of how a pain management system 800 can be trained to develop an individualised pain-management model for a user. Features of FIG. 8 that are also shown in FIG. 1 will be given corresponding reference numbers in the 800 series, and will not necessarily be described in detail again here.

In addition to the features of FIG. 1, the system 800 of FIG. 8 includes a UI controller 826. As will be discussed in detail below, the UI controller 826 is used to modify the functionality of the user interface 802 such that over time the user is presented with additional mechanisms for providing the user-input-parameters 804.

Initially, the user interface 802 may provide the user with a display screen that enables them to enter the user-input-parameters 804 using sliders in the same way that is illustrated in FIG. 2. This can be referred to as a first-user-input-mechanism. The UI controller 826 provides a UI-control-signal to the user interface 802 that instructs the user interface 802 to activate the first-user-input-mechanism such that the user can enter the user-input-parameters 804 using the first-user-input-mechanism.

After the user has entered user-input-parameters 804 for a predetermined number of periods of time (such as a predetermined number of days), or after a predetermined period of time, the UI controller 826 can provide a UI-control-signal to the user interface 802 that instructs the user interface 802 to additionally or alternatively activate a further-user-input-mechanism.

FIG. 9 shows three example screenshots that will be used to describe examples of different user-input-mechanisms.

The first screenshot of FIG. 9 is the same as the second screenshot of FIG. 2, and shows how a user can use sliders to enter the information for the user-input-parameters. As indicated above, this can be referred to as a first-user-input-mechanism. Also shown in the first screenshot is a "Timer" button 928 associated with each of the user-input-parameters. Selection of the "Timer" button 928 can enable the user to access a further-input-mechanism. In this example, the "Timer" button 928 may be deactivated (such that it cannot be selected by the user) until the user has provided user-input-parameters for at least a predetermined number of days (for example at least 3, 4 or 7 days). Such deactivation may be implemented in accordance with a UI-control-signal received from the UI controller 826. In this way, the system 800 can ensure that the user is comfortable with providing information using the first-user-input-mechanism before additional mechanisms are made available to the user. This can enable an improved continued use of the user interface because it can result in the user being able to reliably and accurately provide the required information to the system so that the pain-management-model can be trained effectively.

The second screenshot in FIG. 9 illustrates a display that can be presented to the user after the "Timer" button 928 has been selected. The display of the second screenshot is one example of a further-user-input-mechanism. In this example, the timer can count down from a target-time, which is set by the user as a goal in this implementation. The user interface 802 can then convert the target-time to a duration-characteristic of the associated user-input-parameter once the timer has counted down to zero.

The third screenshot in FIG. 9 illustrates an alternative display that can be presented to the user after the "Timer" button 928 has been selected. The display of the third screenshot is another example of a further-user-input-mechanism. The display of the third screenshot can also be accessed by pressing a "Stopwatch" button 930 that is shown in the second screenshot. In this example, the stopwatch can count up from zero to measure the duration of the associated activity. Once the user stops and saves the stopwatch, the user interface can convert the duration of the stopwatch to a duration-characteristic of the associated user-input-parameter.

A yet further example of a further-user-input-mechanism can be accessed by a user selecting a "Guide" button 932. As shown in the first screenshot, there may be a "Guide" button 932 associated with each of the user-input-parameters. Alternatively, there may be a single "Guide" button that applies to all, or a subset, of the user-input-parameters. If the user selects a "Guide" button 932, then the user interface can pre-populate the information for the associated user-input-parameter (or parameters) based on historic information. For instance, the system may extract historic information for the user-input-parameter (or parameters) from memory (which may be stored as parts of pain-parameters-log-entries as discussed above), and then perform a statistical operation on these historic user-input-parameters to calculate guide-input-parameter values. One example of a simple statistical operation is an averaging operation, such as a mean. Another example of a statistical operation is a mode, such that the value of the user-input-parameter that has been provided most often is offered to the user as a guide. The user can then log the guide-input-parameter values as they are if they do not need changing, or can modify them before submitting them to the AI processor 808 for further processing.

FIG. 10 shows another example embodiment of a pain management system 1000 according to the present disclosure. The pain management system 1000 can be used to train an individualised pain-management model for a user in a similar way to the system of FIG. 1 and/or to help a user predict an expected level of pain based on their planned activities in a similar way to the system of FIG. 5. Features of FIG. 10 that are also shown in an earlier figure will be given corresponding reference numbers in the 1000 series.

The system 1000 of FIG. 10 includes one or more sensors 1036 that can provide (directly or indirectly after pre-processing 1038) one or more sensed-input-parameters 1034 to the user interface 1002. The user interface 1002 can then process the sensed-input-parameters 1034 in the same way as the user-input-parameters 1004 in any of the examples described herein. In some examples the pre-processing 1038, as it is described here, can include a known algorithm that classifies activities based on the sensor signals. For instance, algorithms are known that can identify sleep, rest and physical activities from sensor signals, and can therefore also determine at least a duration associated with those activities for providing to the user interface 1002 as sensed-input-parameters 1034.

The sensed-input-parameters 1034 can be used as additional or alternative inputs by the AI processor 1008 to train a pain-management-model along with a user-input-pain-score 1006 and/or to determine a calculated-pain-score (not shown in FIG. 10) or calculated-user-parameters (also not shown) using a trained model.

Advantageously, the sensors 1036 can be used to automatically gather the information for the input-parameters such that a user does not have to manually enter the information themselves. In this way, the sensed-input-parameters 1034 can be considered as a subset of the user-input-parameters 1004.

The sensors 1036 can be provided as part of a wearable device (such as a smart watch or a fitness/activity tracker) or a user's smartphone. Such devices are known to be able to provide information in relation to various activities, such as a user's sleep, physical activity, rest etc. This activity information (at least some of which can be considered as pre-classified) can be provided to the user interface as sensed-input-parameters 1034 (in some cases following a pre-processing operation 1038). In some examples, when the user interface 1002 receives sensed-input-parameters 1034 it can automatically push a message to the user (for example using the user interface 1002) that requests the user to provide information to populate any characteristics of the activity that have not been provided as part of the sensed-input-parameters 1034. As one example, if a sensed-input-parameter 1034 relates to physical-activity-parameter, then the sensor 1036 may be able to provide a duration-characteristic for the activity but not a satisfaction-characteristic. In which case, the user interface 1002 may provide the user with an opportunity to manually input the satisfaction-characteristic as part of a user-input-parameter 1004.

Also, the sensors 1036 can be used to provide sensed-input-parameters 1034 that relate to properties of a user, such as one or more measured or determined characteristics of the user's body. As non-limiting examples these can include a heart-rate-parameter, a blood-pressure-parameter, a temperature-parameter, etc.

In some examples, a sensed-input-parameter 1034 can include a timestamp. The timestamp can be associated with a start time of an activity/measure property and/or an end time of an activity/measure property. Optionally, the time-stamp can be stored in memory 1013 as part of a pain-parameter-log-entry. In this way, the stored timestamps can be used as part of the processing to identify pain triggers and protectors that is described above. Furthermore, in some examples the timestamp can be part of an input-parameter that is provided as an input to the ANN. In this way the timestamp can influence the training of the pain-management-model, such that it can also be including in subsequent processing to determine a calculated-pain-score or calculated-user-parameters using the trained model.

In addition, in some examples, the AI processor 1008 may receive one or more environmental-input-parameters (not shown) that can potentially influence how the user experiences pain. For example, the environmental-input-parameters may represent one or more of: ambient air temperature, weather conditions, altitude, and location of the user. Such environmental-input-parameters may be provided to the AI processor 1008 by an appropriate sensor. In some examples, one or more of the environmental-input-parameters can be retrieved from an online web service—for instance, a GPS sensor of with a device associated with a user (such as their smartphone) can provide the web service with the location of the user, and the web service can provide one or more environmental-input-parameters (such as weather, temperature, etc.) to the user interface 1002 (or directly to the AI processor 1008) based on the location. Again, the user interface 1002/AI processor 1008 can process such environmental-input-parameters in the same way as the user-input-parameters 1004 in any of the examples described herein.

FIG. 11 illustrates schematically a computer-implemented method according to the present disclosure. The method of FIG. 11 generally corresponds to at least some of the functionality that is described above with reference to FIGS. 3 and 4

At step 1150, the method involves receiving a target-pain-score that represents a level of pain that the user considers acceptable during a defined period of time. At step 1152, the method receives one or more target-input-parameters which represent properties and/or activities of a user during the same defined period of time. In the same way as described above, the one or more target-input-parameters are a subset of a full list of input-parameters that are available. At step 1154, the method receives one or more user-settings that represent one or more input-parameters that the user is looking to increase or decrease. It will be appreciated that it does not matter which order steps 1150, 1152 and 1154 are performed in. Indeed, one or of the steps they be performed at the same time.

At step 1156, the method continues by using a neural network that has been trained for the individual user to determine one or more calculated-user-parameters based on the target-pain-score and the target-input-parameters. As discussed in detail above, at least one of the calculated-user-parameters is set based on the user-settings. Then at step 1158, the method includes presenting the one or more calculated-user-parameters using a user interface. Presenting the calculated-user-parameters in this way can enable a user to change their behaviours/activities in order to improve their health and wellbeing while being able to control the amount of pain that they experience.

In other examples, the general principles that are discussed in detail herein can be applied to applications that are not necessarily associated with pain. Such a system can be referred to as a personal-management system, in that it can be a system that is trained such that it is bespoke to an individual. Such examples can receive a target-score (which is a more generic version of the target-pain-score that is described above) that represents a score/level of a personal-characteristic that the user considers acceptable during a defined period of time. Non-limiting examples of personal-characteristics can include: stress, anxiety, depression, burnout, fatigue, quality of life, long-term coronavirus/COVID (or the long term effects of any other disease or condition), mental health wellbeing, and personal performance (such as in one or more specific activities, including, but not limited to, elite sports).

Clinical Trial

Introduction

Chronic pain is a major health problem world-wide. Over 100 million individuals in USA (Pitcher, M. H., et al. (2019) Prevalence and profile of high-impact chronic pain in the United States. J. Pain 20, 146-160) are suffering and a majority patients find even the most up-to-date treatments falling short due to lack of efficacy or significant side effects. PainDrainer™ is a digital coach for self-management of pain, powered by artificial intelligence, aiming to improve the quality of life (QoL). (The PainDrainer™ tool corresponds to the systems and methods that are described above.) It utilizes the concept of the Acceptance and Commitment Therapy (Twohig M. P. (2012) Introduction: The Basics of Acceptance and Commitment Therapy, Cognitive and Behavioral Practice 19, 499-507), believed to constitute a core component in evidence-based treatment of chronic pain. This trial is study that tests key elements, such as patient acceptance and improvement in QoL.

Method

A one-arm, open label study was performed at the Koman Family Outpatient Pavilion at UC San Diego Health. Fifteen (15) eligible patients (67% women), suffering from neck, shoulder, and/or lower back pain were included after signing an informed consent. The pilot study was performed in two phases, representing different user experience, with 9 patients in the first phase and 6 patients in the second phase, using PainDrainer™ a tool for self-management of pain. PROMIS Pain Interference 6a validated questionnaire was used to measure changes in Pain Interference/Quality of Life and Pain Intensity. From the PROMIS questionnaire, the T-score was calculated. The statistical significance (p-value) between the T-scores was then estimated, using a one-tail, paired T-test. The difference in T-score was also compared to the Minimally Important Difference (MID) seen in pain management (Chen C. X., et al., (2018) Estimating minimally important differences for the PROMIS pain interference scales: results from 3 randomized clinical trials, Pain 159, 775-782).

Results

PainDrainer™ was developed as a tool for self-management of pain in collaboration with health care providers, pain specialists and experts in artificial intelligence and was evaluated in this trial. The frequency of patients in phase one with a positive response was 56% (5/9 patients) and in phase two 83% (5/6 patients). The power in the response was analyzed, using a one-tail, paired T-tests to calculate the statistical difference between T-scores, pre- and posttreatment. In phase one, the p-value was 0.0086 and in phase two the p-value was 0.0014. Primary outcome—patients (10/15) experiencing an increase in QoL are shown in FIG. 12 (improved QoL is labelled with reference 1260, reduced QoL is labelled with reference 1262, and no change is labelled with reference 1264). MID refers to the smallest meaningful difference in T-score that carries implications for the patient and normally ranges between 2 & 34. The difference in T-scores for posttreatment with PainDrainer™ surpassed MID and was 3.0 and 4.8 in phase one and two, respectively (FIG. 13). Secondary outcome—patients (10/15) in the two phases experiencing a reduction in Pain Intensity (PI) are shown in FIG. 14 (reduced pain is labelled with reference 1470, increased pain is labelled with reference 1472, and no change is labelled with reference 1474). The mean reduction in pain intensity was 1.6 units (range 1-4 units).

CONCLUSIONS

PainDrainer™ is the first truly patient-centric device, since it is powered by AI adapting to each patient's need.

PainDrainer™ achieves a clinical significant improvement in quality of life and reduction in pain intensity in chronic pain patients.

PainDrainer™ allowed chronic pain patients to better manage the relation between daily activities and their pain.

The invention claimed is:

1. A pain-management system configured to:

receive a target-pain-score that represents a level of pain that the user considers acceptable during a defined period of time;

receive one or more target-input-parameters which represent properties and/or activities of a user during the same defined period of time, wherein the one or more target-input-parameters are a subset of a full list of input-parameters that are available;

receive one or more settings that represent one or more input-parameters that are to be increased or decreased, and wherein the one or more input-parameters represent one or more activity performed by the user;

compare the received target-pain-score and/or one or more of the target-input-parameters to historical pain-parameter-log-entries, each pain-parameter-log-entry representing user-input-parameters and corresponding user-input-pain-score, to locate a matched-pain-parameter-log-entry;

modify the matched-pain-parameter-log-entry based on the one or more received settings in order to generate a modified-pain-parameters-log-entry;

use a neural network that has been trained for the individual user to determine one or more calculated-user-parameters based on the target-pain-score, the target-input-parameters, and/or the modified-pain-parameters-log-entry, wherein at least one of the calculated-user-parameters is set based on the settings, and wherein the calculated-user-parameters include a calculated-pain-score and/or suggestions for values for one or more of the settings that are expected to achieve the target-pain-score; and present, using a user interface: (i) one or more user-parameters of the modified-pain-parameters-log-entry as the calculated-user-parameters, and (ii) the calculated-pain-score.

2. The system of claim 1, wherein the system is configured to modify the matched-pain-parameters-log-entry to generate the modified-pain-parameters-log-entry by increasing or decreasing one or more user-input-parameters of the matched-pain-parameters-log-entry.

3. The system of claim 1, wherein the system is configured to:

inspect a set of historic pain-parameter-log-entries associated with the user to identify, as a matched-pain-parameters-log-entry, a pain-parameters-log-entry that is a match with the received target-pain-score and the target-input-parameters, wherein each pain-parameter-log-entry represents a plurality of user-input-parameters and a user-input pain-score;

modify the matched-pain-parameters-log-entry based on the settings in order to generate a modified-pain-parameters-log-entry;

apply the neural network to the modified-pain-parameters-log-entry to determine a calculated-pain-score; and compare the calculated-pain-score to the target-pain-score, and:

if the calculated-pain-score is greater than the target-pain-score, then:

adjust one or more of the input-parameters of the modified-pain-parameters-log-entry;

apply the neural network to the adjusted modified-pain-parameters-log-entry to determine an adjusted calculated-pain-score; and repeat the compare step one or more times for the adjusted calculated-pain-score; and if the calculated-pain-score is less than or equal to the target-pain-score, then present using the user interface: (i) one or more user-parameters of the modified-pain-parameters-log-entry as the calculated-user-parameters, and (ii) the calculated-pain-score.

4. The system of claim 3, wherein the system is configured to repeat the compare step a plurality of times up to a predetermined maximum number.

5. The system of claim 1, wherein the system is further configured to:

present to the user via the user interface an option for modifying one or more of the calculated-user-parameters;

receive one or more modified calculated-user-parameters from the user interface representative of user input;

apply the neural network to the modified calculated-user-parameters to determine a modified calculated-pain-score; and present the modified calculated-pain-score using the user interface.

6. The system of claim 1, further comprising:

a user interface configured to receive:

a plurality of user-input-parameters, which represent properties and/or activities of a user during a defined period of time; and a user-input pain-score, which represents a degree of pain experienced by the user during the same defined period of time; and an AI processor configured to:

set a plurality of weighting-values of the neural network based on the plurality of user-input-parameters and the user-input pain-score for the user.

7. The system of claim 6, wherein the system is configured to store the plurality of weighting-values associated with a user-identifier, wherein the user-identifier is uniquely associated with an individual user's profile.

8. The system of claim 6, wherein the system is further configured to:

modify the functionality of the user interface over time such that the user is presented with additional mechanisms for providing the user-input-parameters.

9. The system of claim 6, wherein the user-input-parameters and the target-input-parameters include one or more of the following characteristics:

(i) a duration-characteristic, which represents the duration that the user performed the activity/or exhibited the property;

(ii) an intensity-characteristic, which represents the intensity with which the user performed the activity;

(iii) a satisfaction-characteristic, which represents the degree of satisfaction that the user experienced when performing the activity; and (iv) a type-characteristic.

10. The system of claim 6, wherein the AI processor is configured to store pain-parameters-log-entries in memory, wherein each pain-parameters-log-entry comprises:

the plurality of user-input-parameters;

the user-input-pain-score; and a date-identifier associated with the corresponding user-input-parameters and user-input pain-score.

11. The system of claim 10, wherein each pain-parameters-log-entry further comprises:

a user-identifier that is uniquely associated with an individual user for which the plurality of user-input-parameters and the user-input-pain-score relates.

12. The system of claim 10, wherein the system is configured to determine a pain trigger by:

processing a plurality of pain-parameter-log-entries to identify pain-parameter log-entries that have a user-input pain-score that is increasing as high-pain-parameter-log-entries, wherein each pain-parameter-log-entry comprises one or more user-input-parameters and a user-input pain-score;

perform an analysis of the user-input-parameters of the high-pain parameter-log-entries to determine a correlation-score that represents the degree of correlation between values of corresponding user-input-parameters in the high-pain-parameter-log-entries; and identify one or more user-parameters as a pain trigger if they have a correlation-score that satisfies a correlation-criterion.

13. The system of claim 10, wherein the system is configured to determine a pain protector by:

processing a plurality of pain-parameter-log-entries to identify pain-parameter log-entries that have a user-input pain-score that is decreasing as low-pain-parameter-log-entries, wherein each pain-parameter-log-entry comprises one or more user-input-parameters and a user-input pain-score;

perform an analysis of the user-input-parameters of the low-pain-parameter-log-entries to determine a correlation-score that represents the degree of correlation between values of corresponding user-input-parameters in the low-pain parameter-log-entries; and identify one or more user-parameters as a pain protector if they have a correlation-score that satisfies a correlation-criterion.

14. The system of claim 6, wherein:

the plurality of user-input-parameters comprises one or more sensed-input parameters, wherein the sensed-input-parameters are provided directly or indirectly from a sensor.

15. The system of claim 6, wherein the user-input-parameters comprise one or more of:

a sleep-parameter;

a work-parameter;

a physical-activity-parameter; a housework-parameter;

a leisure-parameter;

a rest-parameter; and a pain-range-parameter;

a heart-rate-parameter;

a blood-pressure-parameter;

a temperature-parameter an energy level/tiredness fatigue parameter; and/or a stress level parameter.

16. A computer-implemented method comprising:

receiving a target-pain-score that represents a level of pain that the user considers acceptable during a defined period of time;

receiving one or more target-input-parameters which represent properties and/or activities of a user during the same defined period of time, wherein the one or more target-input-parameters are a subset of a full list of input-parameters that are available;

receiving one or more settings that represent one or more input-parameters that the user is looking to increase or decrease, and wherein the one or more input-parameters represent one or more activity performed by the user;

comparing the received target-pain-score and/or one or more of the target-input-parameters to historical pain-parameter-log-entries, each pain-parameter-log-entry representing user-input-parameters and corresponding user-input-pain-score, to locate a matched-pain-parameter-log-entry;

modifying the matched-pain-parameter-log-entry based on the one or more received settings in order to generate a modified-pain-parameters-log-entry;

using a neural network that has been trained for the individual user to determine one or more calculated-user-parameters based on the target-pain-score, and the target-input-parameters, and/or the modified-pain-parameters-log-entry, wherein at least one of the calculated-user-parameters is set based on the settings, and wherein the calculated-user-parameters include a calculated-pain-score and/or suggestions for values for one or more of the settings that are expected to achieve the target-pain-score; and presenting (i) one or more user-parameters of the modified-pain-parameters-log-entry as the calculated-user-parameters, and (ii) the calculated-pain-score.

17. A non-transitory computer-readable medium storing instructions that, when executed by a processor, cause the processor to:

receive a target-pain-score that represents a level of pain that the user considers acceptable during a defined period of time;

receive one or more target-input-parameters which represent properties and/or activities of a user during the same defined period of time, wherein the one or more target-input-parameters are a subset of a full list of input-parameters that are available;

receive one or more settings that represent one or more input-parameters that the user is looking to increase or decrease, and wherein the one or more input-parameters represent one or more activity performed by the user;

comparing the received target-pain-score and/or one or more of the target-input-parameters to historical pain-parameter-log-entries, each pain-parameter-log-entry representing user-input-parameters and corresponding user-input-pain-score, to locate a matched-pain-parameter-log-entry;

modifying the matched-pain-parameter-log-entry based on the one or more received settings in order to generate a modified-pain-parameters-log-entry;

use a neural network that has been trained for the individual user to determine one or more calculated-user-parameters based on the target-pain-score, the target-input-parameters, and/or the modified-pain-parameters-log-entry, wherein at least one of the calculated-user-parameters is set based on the settings, and wherein the calculated-user-parameters include a calculated-pain-score and/or suggestions for values for one or more of the settings that are expected to achieve the target-pain-score; and present (i) one or more user-parameters of the modified-pain-parameters-log-entry as the calculated-user-parameters, and (ii) the calculated-pain-score.

* * * * *